United States Patent
Kataoka et al.

(10) Patent No.: US 8,663,929 B2
(45) Date of Patent: Mar. 4, 2014

(54) METHOD FOR DETECTION OF LIVER CANCER CELL USING ANTI-GLYPICAN-3 ANTIBODY

(75) Inventors: Hiroaki Kataoka, Miyazaki (JP); Hirotake Takai, Shizuoka (JP); Atsuhiko Kato, Shizuoka (JP); Masami Suzuki, Shizuoka (JP); Masamichi Sugimoto, Kanagawa (JP)

(73) Assignees: University of Miyazaki, Miyazaki (JP); Chugai Seiyaku Kabushiki Kaisha, Tokyo (JP)

( * ) Notice: Subject to any disclaimer, the term of this patent is extended or adjusted under 35 U.S.C. 154(b) by 261 days.

(21) Appl. No.: 12/736,180

(22) PCT Filed: Mar. 16, 2009

(86) PCT No.: PCT/JP2009/055567
§ 371 (c)(1),
(2), (4) Date: Dec. 17, 2010

(87) PCT Pub. No.: WO2009/116659
PCT Pub. Date: Sep. 24, 2009

(65) Prior Publication Data
US 2011/0091907 A1    Apr. 21, 2011

(30) Foreign Application Priority Data

Mar. 17, 2008 (JP) .................................. 2008-068316

(51) Int. Cl.
*G01N 33/53* (2006.01)
(52) U.S. Cl.
USPC .............................................................. 435/7.1
(58) Field of Classification Search
None
See application file for complete search history.

(56) References Cited

FOREIGN PATENT DOCUMENTS

| EP | 1 674 111 A1 | 6/2006 |
|---|---|---|
| JP | 2000-46827 A | 2/2000 |
| WO | 9113336 A1 | 9/1991 |
| WO | 03-100429 A2 | 12/2003 |
| WO | WO 03/100429 A2 * | 12/2003 |
| WO | 2004-022739 A1 | 3/2004 |
| WO | 2006-006693 A1 | 1/2006 |

OTHER PUBLICATIONS

Tockman et al (Cancer Res., 1992, 52:2711s-2718s).*
Yamauchi et al (Mod Path, 2005, 18(2): 1591-1598).*
Ramos-Vara et al (J Vet Diagn Invest, 2000, 12(4): 307-311).*
European Search Report for counterpart patent application No. EP09722485; issued Jun. 10, 2011.
Yorita, K. et al. "Prognostic significance of circumferential cell surface immunoreactivity of glypican-3 in hepatocellular carcinoma". In: Liver International; vol. 31. No. 1; Jan. 1, 2011; pp. 120-131.

Takai H. et al. "Optimization of tissue processing for immunohistochemistry for the detection of human glypican-3". In: ACTA Histochemica; vol. 112 (1); Jan. 1, 2010; pp. 240-250.
Iglesias, B.V. et al. "Expression pattern of glypican-3 (GPC3) during human embryonic and fetal development". In: Histology and Histopathology: Cellular and Molecular Biology; vol. 23, No. 11: Nov. 1, 2008; pp. 1333-1340.
Ramos-Vara, J.A. et al, "Optimization of immunohistochemical methods using two different antigen retrieval methods on formalin-fixed, paraffin-embedded tissues: experience with 63 markers". In: Journal of Veterinary Diagnostic Investigation; vol. 12, No. 4; Jul. 1, 2000; pp. 307-311.
MacIntyre, N. "Unmasking antigens for immunohistochemistry". In: British Journal of Biomedical Science, Royal Society of Medicine Services; vol. 58, No. 3; Jan. 1, 2001; pp. 190-196.
Perez, E.A. "HER-2 as a prognostic predictive, and therapeutic target in breast cancer". Internet Citation XP007918597; retrieved from URL:http://www.moffitt.org/moffittapps/ccj/v6n3/article1.htm; May 1999; pp. 1-7.
Kandil, D. et al. "Glypican-3 immunocytochemistry in liver fine-needle aspirates". In: Cancer, American Cancer Society; vol. 111, No. 5; Oct. 25, 2007; pp. 316-322.
Capurro, M et al.; Glypican-3: A Novel Serum and Histochemical Marker for Hepatocellular Carcinoma. Gastroenerology; Jul. 2003, vol. 125(1); pp. 89-97.
Yamauchi, N. et al.; The Glypican 3 Oncofetal Protein Is a Promising Diagnostic Marker for Hepatocellular Carcinoma. Modern Pathology; Dec. 2005, vol. 18; pp. 1591-1598.
Libbrecht, L et al.; Glypican-3 Expression Distinguishes Small Hepatocellular Carcinomas From Cirrhosis, Dysplastic Nodules, and Focal Nodular Hyperplasia-Like Nodules. Am J Surg Pathol; Nov. 2006, vol. 30, (11); pp. 1405-1411.
Grozdanov, PN et al.; The Oncofetal Protein Glypican-3 Is a Novel Marker of Hepatic Progenitor/Oval Cells. Laboratory Investigation; Oct. 2006, vol. 86 (12); pp. 1272-1284.
Llovet, JM et al.; A Molecular Signature to Discriminate Dysplastic Nodules From Early Hepatocellular Carcinoma in HCV Cirrhosis. Gastroenterology; Sep. 2006, vol. 131 (6); pp. 1758-1767. Materials and Methods (Immunohistochemistry).
Iwai, M et al.; Antigen Retrieval Methods for Immunostaining Using Paraffin Sections. The Cell; 1997, vol. 29 (9); pp. 348-352.
Hamakawa, S et al.; Antigen Retrieval Methods in Immunostaining. Kensa to Gijyutsu; 2002, vol. 30 (7); pp. 625-632.
Kamoshida, S et al.; Immunohistochemical Demonstration of Dihydropyrimidine Dehydrogenase in Normal and Cancerous Tissues. Acta Histochem Cytochem; 2003, vol. 36 (5); pp. 471-479. Materials and Methods (Immunohistochemistry).

(Continued)

Primary Examiner — Sean Aeder
(74) Attorney, Agent, or Firm — Sughrue Mion, PLLC

(57) ABSTRACT

The present invention relates to an in-vitro immunoassay method for detecting the presence of liver cancer cells in a subject. In the method of the present invention, antigen retrieval treatment based on heat-induced epitope retrieval method and antigen retrieval treatment based on protease-induced epitope retrieval method can be combined in the detection of glypican 3 antigen expression in liver cancer tissues to thereby detect the difference in the expression level or expression pattern of the glypican 3 antigen by immuno-histochemical staining method. This enables samples, which has been determined by the conventional HIER method as highly expressing glypican 3, to be graded according to the expression level of glypican 3.

12 Claims, 6 Drawing Sheets
(4 of 6 Drawing Sheet(s) Filed in Color)

(56) References Cited

OTHER PUBLICATIONS

Budwit-Novotny, DA et al.; Immunohistochemical Analyses of Estrogen Receptor in Endometrial Adenocarcinoma Using a Monoclonal Antibody. Cancer Res; 1986, vol. 46 (10); pp. 5419-5425. Materials and Methods (Scoring of Assays).

Hasegawa, T et al.; Quantitative Immunohistochemical Evaluation of MIB-1 Labeling Index in Adult Soft-Tissue Sarcomas by Computer-Assisted Image Analysis. Patho Int; 2002, vol. 52 (7); pp. 433-437. Materials and Methods (Image analysis).

International Search Report for PCT/JP2009/055567, May 12, 2009.

* cited by examiner

A

B

C

D

A

B

C

D

A

B

C

D

E

F

SEQUENCE LISTING

```
<160> NUMBER OF SEQ ID NOS: 1

<210> SEQ ID NO 1
<211> LENGTH: 580
<212> TYPE: PRT
<213> ORGANISM: homo sapiens

<400> SEQUENCE: 1

Met Ala Gly Thr Val Arg Thr Ala Cys Leu Val Val Ala Met Leu Leu
1               5                   10                  15

Ser Leu Asp Phe Pro Gly Gln Ala Gln Pro Pro Pro Pro Pro Asp
            20                  25                  30

Ala Thr Cys His Gln Val Arg Ser Phe Phe Gln Arg Leu Gln Pro Gly
        35                  40                  45

Leu Lys Trp Val Pro Glu Thr Pro Val Pro Gly Ser Asp Leu Gln Val
    50                  55                  60

Cys Leu Pro Lys Gly Pro Thr Cys Cys Ser Arg Lys Met Glu Glu Lys
65                  70                  75                  80

Tyr Gln Leu Thr Ala Arg Leu Asn Met Glu Gln Leu Leu Gln Ser Ala
                85                  90                  95

Ser Met Glu Leu Lys Phe Leu Ile Ile Gln Asn Ala Ala Val Phe Gln
            100                 105                 110

Glu Ala Phe Glu Ile Val Val Arg His Ala Lys Asn Tyr Thr Asn Ala
        115                 120                 125

Met Phe Lys Asn Asn Tyr Pro Ser Leu Thr Pro Gln Ala Phe Glu Phe
    130                 135                 140

Val Gly Glu Phe Phe Thr Asp Val Ser Leu Tyr Ile Leu Gly Ser Asp
145                 150                 155                 160

Ile Asn Val Asp Asp Met Val Asn Glu Leu Phe Asp Ser Leu Phe Pro
                165                 170                 175

Val Ile Tyr Thr Gln Leu Met Asn Pro Gly Leu Pro Asp Ser Ala Leu
            180                 185                 190

Asp Ile Asn Glu Cys Leu Arg Gly Ala Arg Arg Asp Leu Lys Val Phe
        195                 200                 205

Gly Asn Phe Pro Lys Leu Ile Met Thr Gln Val Ser Lys Ser Leu Gln
    210                 215                 220

Val Thr Arg Ile Phe Leu Gln Ala Leu Asn Leu Gly Ile Glu Val Ile
225                 230                 235                 240

Asn Thr Thr Asp His Leu Lys Phe Ser Lys Asp Cys Gly Arg Met Leu
                245                 250                 255

Thr Arg Met Trp Tyr Cys Ser Tyr Cys Gln Gly Leu Met Met Val Lys
```

```
                    260                 265                 270
Pro Cys Gly Gly Tyr Cys Asn Val Val Met Gln Gly Cys Met Ala Gly
            275                 280                 285

Val Val Glu Ile Asp Lys Tyr Trp Arg Glu Tyr Ile Leu Ser Leu Glu
    290                 295                 300

Glu Leu Val Asn Gly Met Tyr Arg Ile Tyr Asp Met Glu Asn Val Leu
305                     310                 315                 320

Leu Gly Leu Phe Ser Thr Ile His Asp Ser Ile Gln Tyr Val Gln Lys
                325                 330                 335

Asn Ala Gly Lys Leu Thr Thr Thr Ile Gly Lys Leu Cys Ala His Ser
            340                 345                 350

Gln Gln Arg Gln Tyr Arg Ser Ala Tyr Tyr Pro Glu Asp Leu Phe Ile
            355                 360                 365

Asp Lys Lys Val Leu Lys Val Ala His Val Glu His Glu Glu Thr Leu
        370                 375                 380

Ser Ser Arg Arg Arg Glu Leu Ile Gln Lys Leu Lys Ser Phe Ile Ser
385                     390                 395                 400

Phe Tyr Ser Ala Leu Pro Gly Tyr Ile Cys Ser His Ser Pro Val Ala
                405                 410                 415

Glu Asn Asp Thr Leu Cys Trp Asn Gly Gln Glu Leu Val Glu Arg Tyr
                420                 425                 430

Ser Gln Lys Ala Ala Arg Asn Gly Met Lys Asn Gln Phe Asn Leu His
            435                 440                 445

Glu Leu Lys Met Lys Gly Pro Glu Pro Val Val Ser Gln Ile Ile Asp
            450                 455                 460

Lys Leu Lys His Ile Asn Gln Leu Leu Arg Thr Met Ser Met Pro Lys
465                     470                 475                 480

Gly Arg Val Leu Asp Lys Asn Leu Asp Glu Glu Gly Phe Glu Ser Gly
                485                 490                 495

Asp Cys Gly Asp Asp Glu Asp Glu Cys Ile Gly Gly Ser Gly Asp Gly
            500                 505                 510

Met Ile Lys Val Lys Asn Gln Leu Arg Phe Leu Ala Glu Leu Ala Tyr
        515                 520                 525

Asp Leu Asp Val Asp Asp Ala Pro Gly Asn Ser Gln Gln Ala Thr Pro
    530                 535                 540

Lys Asp Asn Glu Ile Ser Thr Phe His Asn Leu Gly Asn Val His Ser
545                     550                 555                 560

Pro Leu Lys Leu Leu Thr Ser Met Ala Ile Ser Val Val Cys Phe Phe
                565                 570                 575

Phe Leu Val His
            580
```

METHOD FOR DETECTION OF LIVER CANCER CELL USING ANTI-GLYPICAN-3 ANTIBODY

TECHNICAL FIELD

The present invention relates to an in-vitro immunoassay method for detecting the presence of liver cancer cells in a subject.

BACKGROUND ART

Since glypican 3 is highly expressed in liver cancer with frequency, the expression profile analysis of glypican 3 in liver cancer is thought to be probably useful for the functional identification of glypican 3 in liver cancer, the treatment or diagnosis of liver cancer, and the prognostic prediction of liver cancer. For the general expression analysis of proteins, immunohistochemistry, particularly, enzyme antibody technique, is widely used in pathological diagnosis. The immunohistochemistry is a method for detecting, highly sensitively and specifically, the presence and distribution of a substance (antigen) in vivo using biological reagents such as antibodies or enzymes. Examples of the features of the immunohistochemistry include: 1. its procedures are convenient; 2. the method is widely applicable in such a way that the obtained biochemical information can be applied to morphological information; 3. the method provides biologically and pathologically important information; and 4. care different from usual methods should be taken because the method uses biological reagents. Moreover, immunohistochemical staining also has the advantage that it can be used in the pathological diagnosis or morphological observation of interest using a wide range of samples such as fresh frozen sections, cytological samples, and paraffin sections of fixed tissues.

Among immunohistochemical methods, immunostaining based on the enzyme antibody technique can utilize formalin-fixed paraffin-embedded tissues used in usual pathological diagnosis and is therefore applied to a very wide range. However, unless sufficient care is taken to, for example, possible artifacts derived from formalin-fixed tissues themselves, not only does staining end unsuccessfully, but also such artifacts sometimes bring about alteration of antigens attributed to formalin fixation and embedding or alteration of antibody penetration or reactivity, resulting in false positive or false negative. Such false positive or false negative may end in misinterpretation of staining results.

Formalin fixation used in usual histological search is useful for maintaining morphology but is not an ideal fixative from the viewpoint of maintaining affinity for antibodies. Thus, alcohol or the like is also used instead of formalin as a fixative. However, a fixation method has not yet been established which is excellent in maintaining morphology and can preserve the affinity of every antigen for antibodies. Accordingly, the formalin fixation is a practical fixation method widely used, although it has a problem in maintaining affinity for antibodies.

Thus, some methods have been proposed for weakening the influence of formalin fixation on the maintenance of affinity for antibodies. A first possible strategy is to select an antibody recognizing an epitope unsusceptible to formalin fixation and use the antibody in immunostaining. Such an antibody recognizing an antigen epitope unsusceptible to formalin fixation, selected from among antibodies recognizing the same epitope can be used in immunostaining to thereby reduce false negative. However, glypican 3 undergoes post-translational modification by protease or the like after being expressed on cell surface and therefore has limitations on epitopes capable of binding to antibodies. Thus, this approach lacks epitope diversity for selecting a suitable epitope.

A second method is to enhance the sensitivity of immunostaining to thereby detect an antigen that cannot be visualized by a usual method. The simplest method is a method which involves adding heavy metal such as copper to DAB (3,3'-diaminobenzidine tetrahydrochloride) usually used for color development in immunostaining. However, this method cannot be expected to significantly increase sensitivity. A method, such as ABC (avidin-biotinylated peroxidase complex) method or LSAB (labeled streptavidin biotinylated antibody) method, has been attempted which involves enhancing sensitivity by repetitively reacting a biotinylated secondary antibody and ABC or enzyme-labeled avidin with sections. However, it has been confirmed that as the number of reactions increases, non-specific background staining also tends to increase. Furthermore, EPOS (enhanced polymer one-step staining) method using an enzyme-labeled dextran polymer or CSA (catalyzed signal amplification) method combining biotinylated tyramide with ABC method has become available, dramatically improving the sensitivity of staining. However, in the detection of antigens in formalin-fixed tissues, the use of the conventional method such as ABC method allows diagnosis of tumor tissues as being positive and normal or non-tumor tissues as being negative, on the basis of which tumor tissues can be differentiated from non-tumor tissues, whereas the use of the highly sensitive method provides detection of even a trace amount of antigens in non-tumor tissues and may therefore fail to make such differentiation depending on the types of antigens. Moreover, the highly sensitive method used also had the problem of increased background staining, because of having high sensitivity.

A third method is to retrieve the reactivity of an antigen whose reactivity with antibodies has been reduced due to formalin fixation. In a method introduced in the 1970s, which involves digesting sections with protease (protease-induced epitope retrieval method; hereinafter, referred to as "PIER method" or "protease-induced epitope retrieval method"), sections are digested with trypsin, pepsin, or the like, prior to immunostaining. This method had such problems as peel-off of sections from glass attributed to the digestion of the sections themselves, and unstable staining results.

Thereafter, heat-induced epitope retrieval method (hereinafter, referred to as "HIER method" or "heat-induced epitope retrieval method") was developed in the 1990s. Heating using a microwave, boiling, or an autoclave allegedly enables an epitope to bind to antibodies as a result of hydrolyzing the antigen by the high-temperature treatment. The expression of glypican 3 in liver cancer has also been detected so far by the HIER method (Non-Patent Documents 1 to 5 and Patent Document 1). However, since anti-glypican 3 antibodies exhibit cross-reactivity with the epithelial cells of blood vessels or hepatic sinusoids, this approach requires such complicated treatment that blocking reaction with a normal liver cell-derived protein lysate is performed in advance to exclude such cross-linking (Non-Patent Document 4). Thus, the HIER method conventionally used cannot accurately detect glypican 3 in liver cancer tissues in such a way that glypican 3 originally expressed on the cell membrane is observed as if this antigen is cytoplasmically expressed (Non-Patent Document 2). Accordingly, an accurate detection method for the expression has been demanded to be developed as a substitute for the conventional HIER method.

[Non-Patent Document 1] Capurro M, Wanless I R, Sherman M, Deboer G, Shi W, Miyoshi E, Filmus J., (2003) Gastroenterology 125 (1), 89-97

[Non-Patent Document 2] Yamauchi N, Watanabe A, Hishinuma M, Ohashi K, Midorikawa Y, Morishita Y, Niki T, Shibahara J, Mori M, Makuuchi M, Hippo Y, Kodama T, Iwanari H, Aburatani H, Fukayama M., (2005) Mod Pathol 18 (12), 1591-8

[Non-Patent Document 3] Libbrecht L, Severi T, Cassiman D, Vander Borght S, Pirenne J, Nevens F, Verslype C, van Pelt J, Roskams T., (2006) Am J Surg Pathol 30 (11), 1405-11

[Non-Patent Document 4] Grozdanov P N, Yovchev M I, Dabeva M D., (2006) Lab Invest 86 (12), 1272-84

[Non-Patent Document 5] Llovet, J. M., Chen, Y., Wurmbach, E., Roayaie, S., Fiel, M. I., Schwartz, M., Thung, S. N., Khitrov, G., Zhang, W., Villanueva, A., Battiston, C., Mazzaferro, V., Bruix, J., Waxman, S., Friedman, S. L., (2006) Gastroenterology 131 (6), 1758-1767

[Patent Document 1] WO2003100429
[Patent Document 2] WO2006006693
[Patent Document 3] WO2004022739

DISCLOSURE OF THE INVENTION

Problems to be Solved by the Invention

The present invention has been achieved in light of such circumstances, and an object of the present invention is to provide a method capable of accurately detecting the expression pattern of glypican 3 in liver cancer tissues.

Means for Solving the Problems

The present inventors have completed the present invention by finding that antigen retrieval treatment based on heat-induced epitope retrieval method and antigen retrieval treatment based on protease-induced epitope retrieval method can be combined in the detection of glypican 3 antigen expression in liver cancer tissues to thereby detect the difference in the expression level or expression pattern of the glypican 3 antigen by immunohistochemical staining method. This enabled samples, which had been determined by the conventional HIER method as highly expressing glypican 3, to be graded according to the expression level of glypican 3.

Specifically, the present application provides the following invention:

[1] an in-vitro immunoassay method for detecting the presence of liver cancer cells in a subject, comprising the steps of:
(a) providing a set of at least two identifiable tissue preparations as paraffin-embedded sections from the same subject, the identifiable tissue preparations being prepared from the subject, then embedded in paraffin and attached to a transparent support;
(b) subjecting the set of the tissue preparations to deparaffinization treatment;
(c) subjecting one of the identifiable tissue preparations in the set treated in the step (b) to antigen retrieval treatment based on heat-induced epitope retrieval method, while subjecting the other tissue preparation to antigen retrieval treatment based on protease-induced epitope retrieval method;
(d) contacting an anti-glypican 3 antibody with the preparations under conditions appropriate for formation of a complex of the anti-glypican 3 antibody with glypican 3 present in the tissue preparations treated in the step (c); and
(e) detecting the presence of the complex, wherein when the complex is present, the subject is diagnosed as having liver cancer cells;

[2] the method according to [1], wherein the heat-induced epitope retrieval method is heating using a microwave;
[3] the method according to [1], wherein the heat-induced epitope retrieval method is heating using an autoclave;
[4] the method according to any of [1] to [3], wherein the protease used in the protease-induced epitope retrieval method is selected from the group consisting of pepsin, trypsin, and protease K;
[5] the method according to any of [1] to [4], wherein detection reaction for detecting the complex is enzymatic reaction;
[6] the method according to any of [1] to [5], wherein the anti-glypican 3 antibody is an antibody binding to a C-terminal polypeptide of glypican 3;
[7] the method according to [6], wherein the C-terminal polypeptide of glypican 3 is a polypeptide consisting of amino acids at positions 359 to 580 described in SEQ ID NO: 1 or a polypeptide consisting of amino acids at positions 375 to 580 therein;
[8] the method according to [6] or [7], wherein the anti-glypican 3 antibody is a GC33 antibody;
[9] the method according to any of [1] to [5], wherein the anti-glypican 3 antibody is a 1G12 antibody;
[10] the method according to any of [1] to [9], wherein in the step (e), the presence of the complex is digitized for detection;
[11] the method according to [10], wherein the digitization is performed by calculation according to the following formula:

$$IR_{Cp}=PR+(SI-Cp)+SP$$

wherein
$IR_{Cp}$ represents an expression level score of glypican 3;
PR represents a numeric value determined by scoring the proportion of cells from which the complex is detected under microscope;
SI–Cp represents a numeric value determined by scoring staining intensity with which the complex is detected in the cytoplasms of cells in the visual field under microscope; and
SP represents a numeric value determined by scoring the proportion of cells that exhibit complete membrane staining in the cell membranes of cells in the visual field under microscope;

[12] the method according to [10], wherein the digitization is performed by calculation according to the following formula:

$$IR_{Cm}=PR+(SI-Cm)+SP$$

wherein
$IR_{Cm}$ represents a membrane localization score of glypican 3;
PR represents a numeric value determined by scoring the proportion of cells from which the complex is detected under microscope;
SI–Cm represents a numeric value determined by scoring staining intensity with which the complex is detected in the cell membranes of cells in the visual field under microscope; and
SP represents a numeric value determined by scoring the proportion of cells that exhibit complete membrane staining in the cell membranes of cells in the visual field under microscope;

[13] a method for classifying liver cancer cells present in a subject on the basis of scores calculated by methods according to [11] and [12];
[14] a method for determining whether or not to administer an anticancer agent containing an anti-glypican 3 antibody to a subject on the basis of scores calculated by methods according to [11] and [12]; and

[15] a method for determining a dose of an anticancer agent containing an anti-glypican 3 antibody in the treatment of liver cancer in a subject on the basis of scores calculated by methods according to [11] and [12].

The patent or application file contains at least one drawing executed in color. Copies of this patent or patent application publication with color drawing(s) will be provided by the Office upon request and payment of the necessary fee.

Figure 1:
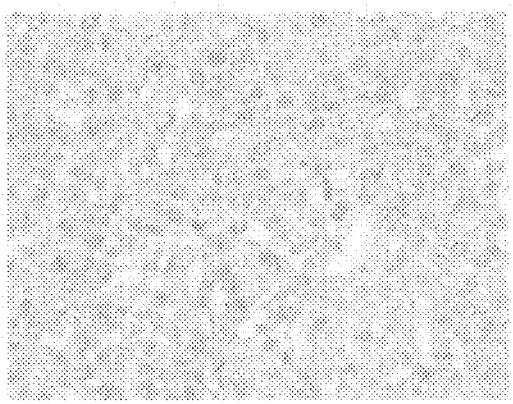
FIG. 1 is a diagram showing each grade of SI scores.
Figure 1:
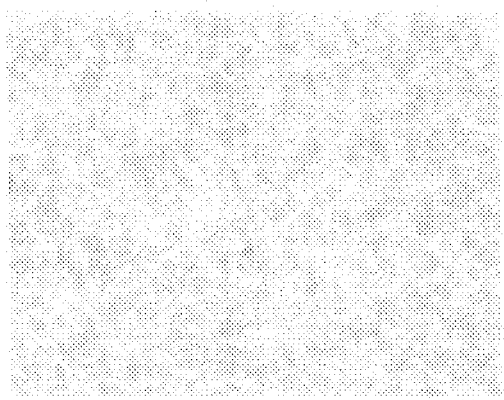
Figure 1:
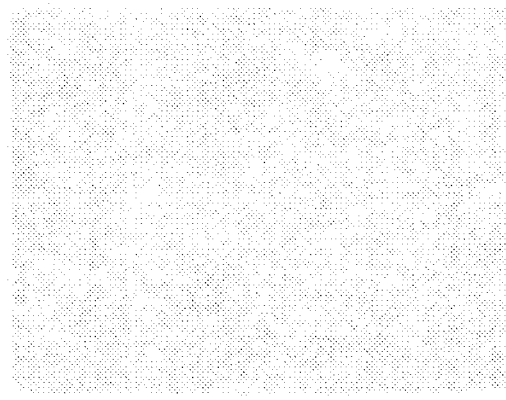
Figure 1:
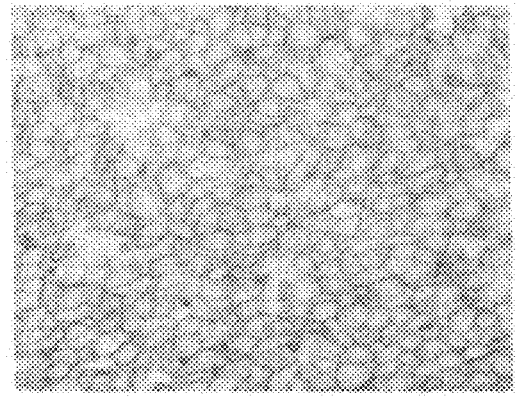

The present specification encompasses the contents described in the specification of Japanese Patent Application No. 2008-068316 that serves as a basis for the priority of the present application.

BEST MODE FOR CARRYING OUT THE INVENTION

Tissue Preparations

The term "tissue preparation" used herein refers to an arbitrary biological preparation obtained from individuals, body fluids (e.g., blood, serum, plasma, and spinal fluid), tissue cultures, or tissue sections, or the like. Preferable examples of the biological preparation used include subject-derived preparations. The subject-derived preparations are preferably tissues obtained from the subject, more preferably the liver tissues of the subject. Biopsy, a method known in the art, is preferably used as a method for collecting the liver tissues. The liver biopsy refers to a method which involves directly inserting a thin long needle into the liver from the skin surface to collect the tissues of the liver. The site of puncture with the needle is usually between ribs in the lower right chest. Before the operation, the safety of the puncture site is confirmed using an ultrasonic examination apparatus, and then, the puncture site is disinfected. Furthermore, the region from the skin to the liver surface is anesthetized, and puncture is performed using a puncture needle after small incision of the skin at the puncture site.

In the present invention, the tissue preparations are observed with a transmitted light under microscope and therefore cut into thin slices to such an extent that the light used in the microscope sufficiently penetrates the tissue preparations. Prior to the cutting into thin slices, the tissue preparations are fixed. Specifically, the tissue preparations are solidified by the dehydration or denaturation of proteins in the tissues/cells to thereby rapidly kill the cells constituting the tissues. The resulting tissues have a stabilized and insolubilized structure. First, the tissue preparations to be fixed are cut using a cutting tool (e.g., surgical knife) into fragments having a size and a shape suitable for preparing paraffin-embedded sections. Subsequently, the fragments are dipped in a fixative, a reagent used for carrying out fixation. The fixative used is preferably formalin, more preferably neutral buffered formalin. The concentration of the neutral buffered formalin is appropriately selected according to the characteristics or physical properties of the tissue preparations. The concentration can be changed appropriately between 1 and 50%, preferably between 5 and 25%, more preferably between 10 and 15%, for use. The fixative containing the tissue preparations dipped therein is appropriately degassed using a vacuum pump. The fixation is carried out by leaving the tissue preparations in the fixative for several hours under conditions involving normal pressure and room temperature. The time required for the fixation can be selected appropriately within the range of 1 hour to 7 days, preferably 2 hours to 3 days, more preferably 3 hours to 24 hours, even more preferably 4 hours to 16 hours. The preparations thus fixed are further appropriately dipped in a phosphate buffer or the like for several hours (the time can be selected appropriately within the range of 2 hours to 48 hours, preferably 3 hours to 24 hours, more preferably 4 hours to 16 hours).

Next, from the fixed tissue preparations, sections can be prepared preferably using frozen section method or paraffin section method. Preferable examples of the frozen section method include a method which involves freezing the tissues by addition into O.C.T. compound (Miles. Inc.) and cutting the frozen tissues into thin slices using a cryostat (frozen section preparing apparatus). In the paraffin section method, the fixed tissue preparations are dipped in an embedding agent, which is then solidified to thereby impart uniform and appropriate hardness to the sections. Paraffin can be used preferably as the embedding agent. The fixed tissue preparations are dehydrated using ethanol. Specifically, the tissue preparations are dehydrated by sequentially dipping the tissue preparations in 70% ethanol, 80% ethanol, and 100% ethanol. The time required for the dipping and the number of dips can be selected appropriately within the ranges of 1 hour to several days and 1 time to 3 times. Moreover, the dipping may be performed at room temperature or at 4° C. For the dipping at 4° C., a longer dipping time (e.g., overnight) is preferable. Subsequently, the liquid phase is replaced by xylene, and then, the tissue preparations are embedded in paraffin. The time required for the replacement of the liquid phase by xylene can be selected appropriately within the range of 1 hour to several hours. In this procedure, the replacement may be performed at room temperature or at 4° C. For the replacement at 4° C., a longer replacement time (e.g., overnight) is preferable. The time required for the paraffin embedding and the number thereof can be selected appropriately within the ranges of 1 hour to several hours and 1 time to 4 times. In this procedure, the embedding may be performed at room temperature or at 4° C. For the embedding at 4° C., a longer embedding time (e.g., overnight) is preferable. Moreover, the tissue preparations can be paraffin-embedded preferably by use of a paraffin embedding apparatus (e.g., EG1160, Leica Microsystems) which automatically processes paraffin embedding reaction.

The tissue preparations thus paraffin-embedded are bonded to a scaffold to prepare a "block", which is then cut using a microtome into thin slices of the desired thickness selected from thicknesses of 1 to 20 μm. The thin tissue sections thus cut are left standing on slide glass as a transparent support for bonding. In this case, slide glass that is coated with 0.01% poly-L-lysine (Sigma-Aldrich Co.) for preventing peel-off of the tissue sections and dried can also be used preferably. The bonded tissue sections are dried in air for an appropriate time selected from between several minutes and 1 hour.

In the present invention, a set of two tissue preparations thus prepared and attached onto the transparent support is prepared. These tissue preparations are preferably two histologically identifiable tissue preparations. The term "identifiable" means that two tissue preparations compared with each other are composed of almost identical cells or tissues in the subject-derived preparation from which the tissue preparations are derived. For example, two tissue preparations prepared as adjacent sections are the two identifiable tissue preparations. In the present invention as well, the "two identifiable tissue preparations" refer to two tissue preparations prepared as adjacent sections, unless otherwise specified. In addition, two tissue preparations that are not prepared as adjacent sections but are composed of cells or tissues whose constructions are identifiable between the two tissue preparations are applicable to the "two identifiable tissue preparations". Preferable examples of the two tissue preparations that are composed of cells or tissues whose constructions are identifiable between the two tissue preparations include: (1) sections containing cells derived from identical cells located at identical positions on the plane coordinates in the tissue sections; and (2) sections whose proportion, of such cells present at identical positions on the plane coordinates is at least 50% or higher, preferably 60% or higher, more preferably 70% or higher, even more preferably 80% or higher, further preferably 90% or higher, particularly preferably 95% or higher.

Antigen Retrieval

In the method of the present invention, the reactivity of an antigen whose reactivity has been reduced due to formalin fixation is retrieved. In the present invention, protease-induced epitope retrieval method (PIER method) is applied to one of the two tissue preparations, while heat-induced epitope retrieval method (HIER method) is applied to the other preparation. Then, the difference in the degree of staining between them after antibody reaction is digitized.

The heat-induced epitope retrieval method appropriately utilizes heating method using a microwave, heating method using an autoclave, or heating method based on boiling treatment, or the like. When the boiling treatment is performed at an output of 780 W to keep the temperature of the solution at approximately 98° C., the time required for the retrieval including the treatment is appropriately selected from between 5 minutes and 60 minutes and is, for example, 10 minutes. The antigen retrieval treatment can be performed in a 10 mM sodium citrate buffer as well as commercially available Target Retrieval Solution (DakoCytomation) or the like. In Examples described later, the Target Retrieval Solution is used. Any buffer or aqueous solution is preferably used as long as an epitope in the antigen recognized by an anti-glypican 3 antibody acquires affinity for the antibody as a result of retrieval treatment such that an antigen-antibody complex described later can be detected.

The protease used in the protease-induced epitope retrieval method is not particularly limited in its type or origin, and generally available protease can be selected appropriately for use. Preferable examples of the protease used include pepsin with a concentration of 0.05% in 0.01 N hydrochloric acid, trypsin with a concentration of 0.1% further containing 0.1% $CaCl_2$ in a Tris buffer (pH 7.6), and protease K with a concentration of 1 to 50 µg/ml in a 10 mM Tris-HCl buffer (pH 7.8) containing 10 mM EDTA and 0.5% SDS. Furthermore, when the protease K is used, the pH of its reaction solution is appropriately selected from between 6.5 and 9.5 and SH reagent or a trypsin or chymotrypsin inhibitor may be used appropriately. Protease included in Histofine Her2 kit (MONO) (Nichirei Bioscience) described in Examples of the present specification is also included in such specific examples of preferable protease. The protease-induced epitope retrieval is usually performed at 37° C. However, the reaction temperature can be changed appropriately within the range of 25° C. to 50° C. When the protease-induced epitope retrieval is, performed at 37° C., the reaction time is appropriately selected from between, for example, 1 minute and 5 hours and is, for example, 15 minutes, 30 minutes, 45 minutes, 1 hour, 2 hours, 3 hours, or 4 hours. After the completion of the retrieval treatment, the tissue preparations thus treated are washed with a wash buffer. PBS (phosphate-buffered saline) is preferably used as the wash buffer. In addition, a Tris-HCl buffer can also be used preferably. The washing conditions usually adopt a method involving performing washing at room temperature for 5 minutes three times. However, the washing time and temperature can be changed appropriately.

Anti-Glypican 3 Antibody

Any anti-glypican 3 antibody can be used preferably in the method of the present invention as long as the antibody has the activity of binding to glypican 3. Particularly preferable examples of the antibody include a GC33 antibody (Patent Document 2) and a 1G12 antibody (Patent Document 1) disclosed in Examples below. Moreover, in addition to these antibodies known in the art, the anti-glypican 3 antibody preferably used in the present invention can be obtained by immunizing non-human animals with glypican 3 as an immunizing antigen. Methods for preparing such anti-glypican 3 antibodies are described in Patent Documents 1 and 2, and those skilled in the art can appropriately obtain the desired anti-glypican 3 antibody on the basis of the methods.

The binding of the anti-glypican 3 antibody to glypican 3 can be detected preferably by a method generally known by those skilled in the art. For example, ELISA (enzyme-linked immunosorbent assay), EIA (enzyme immunoassay), RIA (radioimmunoassay), or fluoroimmunoassay can be used. These methods are described in the general textbook "Antibodies A Laboratory Manual. Ed Harlow, David Lane, Cold Spring Harbor Laboratory, 1988".

Examples of a method for assaying the binding activity of the antibody to cells expressing the antigen include methods described in p. 359-420 in Antibodies A Laboratory Manual. (Ed Harlow, David Lane, Cold Spring Harbor Laboratory, 1988). Specifically, the binding activity can be evaluated preferably according to the principles of ELISA or FACS (fluorescence activated cell sorting) with the cells as an antigen. In the ELISA format, the binding activity of the antibody to the cells is quantitatively evaluated by comparing the levels of signals formed through enzymatic reaction. Specifically, cells forced to express the antigen are immobilized on an ELISA plate, to which test antibodies are then added. Cell-bound antibodies are detected using enzyme-labeled antibodies recognizing the test antibodies. Alternatively, in FACS, dilution series of test antibodies are prepared, and their antibody titers to cells forced to express the antigen can be determined to thereby compare thereamong binding activity to the cells.

The FACS format can assay an antigen expressed on the surface of carrier (e.g., ELISA plate)-unbound cells suspended in a buffer or the like as well as the binding of the antibody to the antigen. Examples of a flow cytometer used in such assay include: FACSCanto™ II, FACSAria™, FACSArray™, FACSVantage™ SE, and FACSCalibur™ (all BD Biosciences); and EPICS ALTRA HyPerSort, Cytomics FC 500, EPICS XL-MCL ADC, EPICSXL ADC, and Cell Lab Quanta/Cell Lab Quanta SC (all Beckman Coulter).

One preferable example of the method for assaying the binding activity of the anti-glypican 3 antibody to the antigen includes a method using secondary antibodies recognizing test antibodies reacted with cells expressing glypican 3. Specifically, cells expressing glypican 3 are reacted with test antibodies and stained with FITC-labeled secondary antibodies, followed by assay using FACSCalibur (BD Biosciences). The obtained fluorescence intensity is analyzed using CELL QUEST Software (BD Biosciences). According to this method, the binding activity of the antibody to the antigen can be determined by: analyzing, using CELL QUEST Software, the fluorescence intensity obtained in FACSCalibur assay; and comparing the geometric mean value (subject Geo-Mean value) obtained by this procedure, with a control Geo-Mean value obtained using a control antibody as a primary antibody. A calculation formula to determine the Geo-Mean values (geometric mean) is described in CELL QUEST Software User's Guide (BD biosciences).

Reaction of Tissue Preparations with Anti-Glypican 3 Antibody

The tissue preparation subjected to the antigen retrieval treatment based on the heat-induced epitope retrieval method and the tissue preparation subjected to the antigen retrieval treatment based on the protease-induced epitope retrieval method are reacted with the anti-glypican 3 antibody as a primary antibody. This reaction is carried out under conditions appropriate for recognition of an epitope in the antigen by the anti-glypican 3 antibody and formation of an antigen-antibody complex. The reaction is usually performed overnight at 4° C. or at 37° C. for 1 hour. However, the reaction conditions can be changed appropriately within a range appropriate for recognition of an epitope in the antigen by the antibody and formation of an antigen-antibody complex. For example, the reaction temperature can be changed within the range of 4° C. to 50° C., and the reaction time can be changed between 1 minute and 7 days. For the reaction at low temperatures, a longer reaction time is preferable. After the completion of the primary antibody reaction, the tissue preparations are washed with a wash buffer. PBS (phosphate-buffered saline) is preferably used as the wash buffer. In addition, a Tris-HCl buffer can also be used preferably. The washing conditions usually adopt a method involving performing washing at room temperature for 5 minutes three times. However, the washing time and temperature can be changed appropriately.

Subsequently, the tissue preparations subjected to the primary antibody reaction are reacted with a secondary antibody recognizing the primary antibody. A secondary antibody labeled in advance with a labeling material for visualizing the secondary antibody is usually used. Preferable examples of the labeling material include: fluorescent dyes such as FITC (fluorescein isothiocyanate), Cy2 (Amersham Biosciences), and Alexa488 (Molecular Probes, Inc.); enzymes such as peroxidase and alkaline phosphatase; and colloidal gold.

The reaction with the secondary antibody is carried out under conditions appropriate for formation of an antigen-antibody complex by the anti-glypican 3 antibody and the secondary antibody recognizing the anti-glypican 3 antibody. The reaction is usually performed at room temperature or 37° C. for 30 minutes to 1 hour. However, the reaction conditions can be changed appropriately within a range appropriate for formation of an antigen-antibody complex by the anti-glypican 3 antibody and the secondary antibody. For example, the reaction temperature can be changed within the range of 4° C. to 50° C., and the reaction time can be changed between 1 minute and 7 days. For the reaction at low temperatures, a longer reaction time is preferable. After the completion of the secondary antibody reaction, the tissue preparations are washed with a wash buffer. PBS (phosphate-buffered saline) is preferably used as the wash buffer. In addition, a Tris-HCl buffer can also be used preferably. The washing conditions usually adopt a method involving performing washing at room temperature for 5 minutes three times. However, the washing time and temperature can be changed appropriately.

Next, the tissue preparations subjected to the secondary antibody reaction are reacted with a substance for visualizing the labeling material. When peroxidase is used as the labeling material for the secondary antibody, the tissue preparations are incubated with a reaction solution obtained by mixing, immediately before the incubation, equal amounts of a 0.02% aqueous hydrogen peroxide solution and a DAB (diaminobenzidine) solution adjusted to a concentration of 0.1% with a 0.1 M Tris-HCl buffer (pH 7.2). In addition to DAB, chromogenic substrates such as DAB-Ni and AEC+ (all DAKO) can be selected appropriately. During the course of incubation, the degree of color development is observed under microscope at intervals. At the point in time when appropriate color development is confirmed, the visualization reaction is terminated by dipping the tissue preparations in PBS.

When alkaline phosphatase is used as the labeling material for the secondary antibody, the tissue preparations are incubated with a BCIP (5-bromo-4-chloro-3-indolyl phosphate)/NBT (nitro blue tetrazolium) (Zymed Laboratories Inc.) substrate solution (NBT at a concentration of 0.4 mM and BCIP at a concentration of 0.38 mM are dissolved in a 50 mM sodium carbonate buffer (pH 9.8) containing 10 mM $MgCl_2$ and 28 mM NaCl). Moreover, in addition to BCIP and NBT, Permanent Red, Fast Red, or Fuchsin+ (all DAKO) may be used appropriately. Prior to the incubation, the tissue preparations may be preincubated at room temperature for 1 minute to several hours with a 0.1 M Tris-HCl buffer (pH 9.5) containing levamisole chloride (inhibitor for endogenous alkaline phosphatase; Nacalai Tesque) at a concentration of 1 mM, 0.1 M sodium chloride, and 50 mM magnesium chloride. During the course of incubation, the tissue preparations are observed under microscope at intervals. At the point in time when the deposits of purple formazan, a final reaction product, are observed, the reaction is terminated by washing the tissue preparations with water or adding TBS containing 2% polyvinyl alcohol. Then, the tissue preparations are washed with TBST (TBS containing 0.1% Tween 20). When colloidal gold is used as the label for the secondary antibody, the colloidal gold is visualized by attaching metallic silver to the gold particles by silver enhancement. The silver enhancement method is generally known by those skilled in the art.

When any of fluorescent dyes such as FITC (fluorescein isothiocyanate), Cy2 (Amersham Biosciences), and Alexa488 (Molecular Probes, Inc.) is used as the labeling material for the secondary antibody, the visualizing substance reaction step is unnecessary. A light emitted by irradiation with a light at the excitation wavelength of the fluorescent material can be detected appropriately by use of a fluorescence microscope.

Classification of Liver Cancer Tissues and Prediction of Therapeutic Effect

Glypican 3 is known to release its N-terminal moiety into serum upon digestion in liver cancer tissues (Patent Document 3). Thus, when an antibody binding to such an N-terminal partial peptide of glypican 3 released into serum upon digestion is used in the method of the present invention, this antibody cannot bind to the C-terminal partial polypeptide that is still anchored on cell surface after undergoing digestion. On the other hand, when an antibody binding to the C-terminal partial peptide is used in the method of the present invention, this antibody can bind to the C-terminal partial polypeptide that is still anchored on cell surface after undergoing digestion. Specifically, the anti-glypican 3 antibody used in the present invention can be selected appropriately according to purposes to thereby achieve both the detection of the partial polypeptide of glypican 3 anchored on cell surface, regardless of whether or not to undergo digestion, and the detection of the partial polypeptide of glypican 3 that is anchored on cell surface before being digested and released into serum upon digestion.

Anti-glypican 3 antibodies have been found to be useful for the treatment and prevention of liver cancer (Patent Document 3). Cell-killing activity exhibited by such a therapeutic anti-glypican 3 antibody is mainly exerted by antibody-dependent cytotoxic activity (ADCC activity) or complement-dependent cytotoxic activity (CDC activity) that is initiated by the binding of effector cells or complements with the Fc domain of the anti-glypican 3 antibody bound with the C-terminal partial polypeptide anchored on cell surface. Thus, when the therapeutic effect of the therapeutic anti-glypican 3 antibody on liver cancer is predicted from the viewpoint of whether or not an epitope bound by the anti-glypican 3 antibody is present in liver cancer tissues, the anti-glypican 3 antibody binding to the C-terminal partial polypeptide can be used preferably in the method of the present invention.

It has been suggested that the digestion site of glypican 3 in liver cancer tissues is the polypeptide bond between amino acids at positions 358 and 359 of the glypican 3 molecule represented by SEQ ID NO: 1 or between amino acids at positions 374 and 375 thereof (Patent Document 3). Thus, examples of the anti-glypican 3 antibody binding to the C-terminal partial polypeptide, preferably used in the present invention include antibodies binding to a polypeptide consisting of amino acids at positions 359 to 580 of the glypican 3 molecule represented by SEQ ID NO: 1 or a polypeptide consisting of amino acids at positions 375 to 580 thereof.

On the other hand, when the therapeutic effect of the therapeutic anti-glypican 3 antibody is predicted from the viewpoint of maturity of the glypican 3 molecule, the anti-glypican 3 antibody binding to the N-terminal partial polypeptide can be used in the method of the present invention. In this case, a glypican 3 molecule recognized by the anti-glypican 3 antibody binding to the N-terminal partial polypeptide can be characterized as a more immature therapeutic target molecule, and liver cancer cells expressing such a glypican 3 molecule can be characterized as more immature therapeutic target cells. The anti-glypican 3 antibody binding to the C-terminal partial polypeptide of the glypican 3 molecule detects the glypican 3 molecule, regardless of the degree of maturity. On the other hand, the anti-glypican 3 antibody binding to the N-terminal partial polypeptide of the glypican 3 molecule detects an immature glypican 3 molecule but does not detect a matured glypican 3 molecule. Specifically, glypican 3 molecules detected by the method of the present invention and liver cancer cells expressing such glypican 3 molecules can be classified on the basis of the degree of maturity by use of two antibodies, i.e., the antibody binding to the C-terminal partial polypeptide of the glypican 3 molecule and the antibody binding to the N-terminal partial polypeptide.

Hereinafter, this classification method will be described more specifically. Two antibodies, i.e., the anti-glypican 3 antibody binding to the C-terminal partial polypeptide of the glypican 3 molecule and the anti-glypican 3 antibody binding to the N-terminal partial polypeptide of the glypican 3 molecule, are prepared as primary antibodies. Two tissue preparations are prepared from the same subject, one of which is reacted with the anti-glypican 3 antibody binding to the N-terminal partial polypeptide of the glypican 3 molecule as a primary antibody and the other tissue preparation of which is reacted with the anti-glypican 3 antibody binding to the C-terminal partial polypeptide of the glypican 3 molecule as another primary antibody. A glypican 3 molecule detected using the anti-glypican 3 antibody binding to the N-terminal partial polypeptide of the glypican 3 molecule can be evaluated as a more immature molecule from the viewpoint of the degree of its maturity, and liver cancer cells expressing such a glypican 3 molecule can be evaluated as more immature cells. Moreover, a glypican 3 molecule that cannot be detected using the anti-glypican 3 antibody binding to N-terminal partial polypeptide of the glypican 3 molecule but is detected using the anti-glypican 3 antibody binding to the C-terminal partial polypeptide of the glypican 3 molecule can be evaluated as a more mature molecule from the viewpoint of the degree of its maturity, and liver cancer cells expressing such a glypican 3 molecule can be evaluated as more mature cells.

When the anti-glypican 3 antibody binding to the N-terminal partial polypeptide of the glypican 3 molecule and the anti-glypican 3 antibody binding to the C-terminal partial polypeptide of the glypican 3 molecule belong to antibody subclasses different from each other or are produced from animals of different kinds, assay can be conducted using one tissue preparation. In this case, a secondary antibody recognizing the anti-glypican 3 antibody binding to the N-terminal partial polypeptide and a secondary antibody recognizing the anti-glypican 3 antibody binding to the C-terminal partial polypeptide are labeled with enzymes or fluorescences of different kinds. As a result, these two anti-glypican 3 antibodies can be used in detection on one tissue preparation.

Digitization of Reactivity with Anti-Glypican 3 Antibody

The present invention provides a method for digitizing the difference in the degree and pattern of detection under microscope of an antigen-antibody complex formed from glypican 3 and an anti-glypican 3 antibody, on the basis of the difference between antigen retrieval reactions (i.e., heat-induced epitope retrieval method and protease-induced epitope retrieval method).

In one aspect, the digitization is performed according to the following formula (1):

$$IR_{Cp} = PR + (SI - Cp) + SP$$

wherein $IR_{Cp}$ represents an expression level score of glypican 3;

PR represents a numeric value determined by scoring the proportion of cells from which the complex is detected under microscope;

SI–Cp represents a numeric value determined by scoring staining intensity with which the complex is detected in the cytoplasms of cells in the visual field under microscope; and SP represents a numeric value determined by scoring the proportion of cells that exhibit complete membrane staining in the cell membranes of cells in the visual field under microscope.

The PR scores are calculated such that: (a) in the visual field under microscope using an objective lens with a magnification of 4 or 10, (i) when the proportion of cells from which the complex is detected is zero, the score of the sample is 0,
(ii) when this proportion is lower than 20%, the score of the sample is 1,
(iii) when this proportion is equal to or higher than 20% and lower than 50%, the score of the sample is 2, and
(iv) when this proportion is equal to or higher than 50%, the score of the sample is 3.

The SI–Cp scores are calculated such that: (b) in the cytoplasms of cells in the visual field under microscope,
(i) when the proportion of cells from which the complex is detected is zero using an objective lens with a magnification of 4 or 10 in the microscope, the score of the sample is 0,
(ii) when positive response, albeit obscure, is slightly observed using an objective lens with a magnification of 10 in the microscope, the score of the sample is 1,
(iii) when positive response is slightly observed using an objective lens with a magnification of 4, the score of the sample is 2,
(iv) when positive response is sufficiently recognizable even using an objective lens with a magnification of 4, the score of the sample is 3, and
(v) when strong positive response is clearly recognized and observed using an objective lens with a magnification of 4, the score of the sample is 4.

The SP scores are calculated such that: (c) in the detection of the complex in the cell membranes of cells in the visual field under microscope,
(i) when the cell membranes exhibit no positive response, the score of the sample is 0,
(ii) when less than 20% of cells exhibiting positive response exhibit complete membrane staining, the score of the sample is 1,
(iii) when 20% or more and less than 50% of cells exhibiting positive response exhibit complete membrane staining, the score of the sample is 2, and
(iv) when 50% or more of cells exhibiting positive response exhibit complete membrane staining, the score of the sample is 3.

In another aspect, the digitization is performed by calculation according to the following formula (2):

$$IR_{Cm} = PR + (SI-Cm) + SP$$

wherein
$IR_{Cm}$ represents a membrane localization score of glypican 3;
PR represents a numeric value determined by scoring the proportion of cells from which the complex is detected under microscope;
SI–Cm represents a numeric value determined by scoring staining intensity with which the complex is detected in the cell membranes of cells in the visual field under microscope; and
SP represents a numeric value determined by scoring the proportion of cells that exhibit complete membrane staining in the cell membranes of cells in the visual field under microscope.

The PR scores are calculated such that: (a) in the visual field under microscope using an objective lens with a magnification of 4 or 10,
(i) when the proportion of cells from which the complex is detected is zero, the score of the sample is 0,
(ii) when this proportion is lower than 20%, the score of the sample is 1,
(iii) when this proportion is equal to or higher than 20% and lower than 50%, the score of the sample is 2, and
(iv) when this proportion is equal to or higher than 50%, the score of the sample is 3.

The SI–Cm scores are calculated such that: (b) in the cell membranes of cells in the visual field under microscope,
(i) when the proportion of cells from which the complex is detected is zero using an objective lens with a magnification of 4 or 10 in the microscope, the score of the sample is 0,
(ii) when positive response, albeit obscure, is slightly observed using an objective lens with a magnification of 10 in the microscope, the score of the sample is 1,
(iii) when positive response obscure to an objective lens with a magnification of 4 but sufficiently recognizable using an objective lens with a magnification of 10 is observed, the score of the sample is 2,
(iv) when positive response is sufficiently recognizable even using an objective lens with a magnification of 4, the score of the sample is 3,
(v) when strong positive response is clearly recognized and observed using an objective lens with a magnification of 4, the score of the sample is 4.

The SP scores are calculated such that: (c) in the detection of the complex in the cell membranes of cells in the visual field under microscope,
(i) when the cell membranes exhibit no positive response, the score of the sample is 0,
(ii) when less than 20% of cells exhibiting positive response exhibit complete membrane staining, the score of the sample is 1,
(iii) when 20% or more and less than 50% of cells exhibiting positive response exhibit complete membrane staining, the score of the sample is 2, and
(iv) when 50% or more of cells exhibiting positive response exhibit complete membrane staining, the score of the sample is 3.

In this case, the scores calculated on the basis of the formulas (1) and (2) are determined for each of the tissue preparation subjected to the heat-induced epitope retrieval method and the tissue preparation subjected to the protease-induced epitope retrieval method. The score calculated on the basis of the formula (1) is a score reflecting the expression level of glypican 3. The score calculated on the basis of the formula (2) is a score reflecting the localization of glypican 3 expression in the cell membrane. The digitization method of the present invention enables liver cancer cells present in a subject to be classified on the basis of the expression level or expression pattern of glypican 3. As shown in Examples below, it was confirmed that the classification is effectively carried out using tissue preparations actually collected from liver cancer patients. It was further confirmed that the classification is also effectively carried out in liver cancer animal models in which HuH-7 or HepG2, a liver cancer cell strain whose glypican 3 expression level has been determined, is transplanted.

In the present invention, results of administering a therapeutic anti-glypican 3 antibody to liver cancer animal models further demonstrated that the difference in the expression level and expression pattern of glypican 3 in liver cancer classified by digitization according to the method of the present invention correlates with the difference in the therapeutic effect of the therapeutic anti-glypican 3 antibody on liver cancer. Specifically, it was shown that the difference in the therapeutic effect of the therapeutic anti-glypican 3 antibody is determined on the basis of the difference in scores digitized according to the present invention. The digitization method according to the present invention provides prediction of the therapeutic effect of a therapeutic agent for liver cancer containing an anti-glypican 3 antibody as an active ingredient, on liver cancer. Moreover, the digitization method according to the present invention can determine the required dose of the therapeutic anti-glypican 3 antibody necessary for obtaining the desired effect in the treatment of liver cancer using the anti-glypican 3 antibody.

EXAMPLES

Hereinafter, the present invention will be described more specifically with reference to Examples. However, the present invention is not intended to be limited to these Examples.

Example 1

Immunostaining of Glypican 3 Using Mouse Models in which Human Liver Cancer Cell Strain Expressing Glypican 3 was Subcutaneously Transplanted into the Abdominal Region (1) Cell Strain The liver cancer cell strains used were HuH-7 cells (Health Science Research Resources Bank, HSRRB) and HepG2 cells (ATCC). HuH-7 was maintained and subcultured in Dulbecco's Modified Eagle's Medium (SIGMA-ALDRICH CO.) containing 10% FBS (BIONET). HepG2 was maintained and subcultured in Minimum Essential Medium Eagle medium (SIGMA-ALDRICH CO.) containing 10% FBS, 1 mmol/L MEM Sodium Pyruvate (Invitrogen Corp.), and 1 mmol/L MEM Non-Essential Amino Acid (Invitrogen Corp.).

(2) Measurement of GPC3 Expression Level (2-1) Measurement Method

The GPC3 expression levels of the HuH-7 and HepG2 cells were measured using a mouse anti-human GPC3 monoclonal antibody (clone name: GC33, described in WO2006/006693) and QIFI-Kit (DakoCytomation). The measurement method was conducted according to a method described in the instruction included therein.

The GC33 antibody used was dissolved at room temperature and then adjusted to 1 mg/ml with PBS. One vial of mIgG2a in a lyophilized state was dissolved in 500 μl of "Japanese Pharmacopoeia Otsuka Distilled Water for Injection" and used as a negative control. $5 \times 10^5$ cells of each strain were suspended in 98 μl of a cell wash solution CellWASH (Becton, Dickinson and Company) supplemented with 0.5 w/v % BSA (Sigma-Aldrich Co.) (hereinafter, referred to as FACS-PBS). Each suspension was supplemented with 2 μl of GC33 or 5 μl of mIgG2a and left standing at 4° C. for 30 minutes. Then, each suspension was supplemented with 1 ml of FACS-PBS and centrifuged at 5000 rpm at 4° C. for 1 minute to fractionate the cells. These cells were resuspended in 98 μl of FACS-PBS.

Moreover, the following procedures were also performed in parallel with the procedures described above: 1 ml of FACS-PBS was added to 100 μl of calibration beads and setup beads included in QIFIKIT, which were then washed by centrifugation at 5000 rpm at 4° C. for 1 minute. The beads were suspended in 98 μl of FACS-PBS. The cells and the beads were separately supplemented with 2 μl of an FITC-labeled goat anti-mouse antibody included in QIFIKIT and subjected to reaction at 4° C. for 45 minutes. Next, each reaction solution was supplemented with 1 ml of FACS-PBS and centrifuged at 5000 rpm at 4° C. for 1 minute. The precipitated cells and beads were separately suspended in 1 ml of FACS-PBS. A fully automatic cell analyzer EPICS-XL (Beckman Coulter) was used to adjust the output such that two peaks formed by the measurement of the labeled setup beads were placed within the monitor. The mean fluorescence intensity (MFI) value of each fluorescence emitted by the cell sample containing the reacted GC33 antibody, the cell sample containing the reacted mIgG2a, and the calibration beads was measured using the fully automatic cell analyzer EPICS-XL. On the basis of five MFI values and antibody-binding capacity (ABC) values of the calibration beads, the optimal straight line was drawn using Microsoft Office Excel 2003 SP2 (Microsoft Corporation). The MFI value of each cell sample was assigned to this straight line of calibration to determine its ABC value. A value determined by subtracting the ABC value of the sample containing the reacted mIgG2a from that of the sample containing the reacted GC33 antibody was used as the number of antibody-binding sites.

As a result, the expression level of glypican 3 in HuH-7 was $1.25 \times 10^5$ molecules per cell. The expression level of glypican 3 in HepG2 was $9.67 \times 10^5$ molecules per cell.

(3) Preparation of Mouse Models in which Human Liver Cancer Cell Strain was Subcutaneously Transplanted into the Abdominal Region HuH-7 and HepG2 cells were separately adjusted to $5 \times 10^7$ cells per ml with a solution containing equal amounts of the medium for maintenance and subculture thereof described in the paragraph (1) and MATRIGEL Matrix (BD Biosciences). One day before the transplantation of each cell strain into mice, 100 μl of an anti-asialo GM1 antibody (Wako Pure Chemical Industries, Ltd.; 1 vial of the contents was dissolved in 1 ml of distilled water and further diluted with 4 ml of saline) was intraperitoneally administered in advance to 5-week-old male SCID mice (CLEA Japan, Inc.). The anti-asialo GM1 antibody (Wako Pure Chemical Industries, Ltd.) was prepared by dissolving 1 vial of the contents in 1 ml of distilled water and further diluting the solution with 4 ml of saline. On the next day, 100 μl of each cell suspension (i.e. $5 \times 10^6$ cells per mouse) was subcutaneously transplanted into the abdominal regions of the mice.

(4) Study on Method for Preparing Tumor Tissue Sections

Uniform tissue grafts collected from the HepG2-transplanted models prepared in the paragraph (3) were quadrisected using a surgical knife. Among them, one fragment was fixed in 10% neutral buffered formalin for 24 hours. The fixed tissue slice was then embedded in paraffin using an automatic embedding apparatus ETP-150C (Sakura Finetek Japan Co., Ltd.) and stored at 4° C. (method A).

Next, a different fragment was fixed at 4° C. for 6 hours using a PLP fixative ($NaIO_4$ at a concentration of 10 mM, lysine at a concentration of 75 mM, phosphate buffer at a concentration of 37.5 mM, paraformaldehyde at a concentration of 2%) containing 4% paraformaldehyde and then washed with PBS (phosphate-buffered saline, 10 mM, pH 7.4) at 4° C. Subsequently, the fragment was dehydrated in acetone overnight at 4° C. and at room temperature for 2 hours. The fragment was further purified with methyl benzoate for 1 hour and with xylene for 1 hour, then embedded in paraffin in the same way as above and stored at 4° C. (method B).

The paraffin-embedded preparations prepared in the methods A and B were cut on a cryostat microtome into thin slices immediately before being applied to immunohistological staining. The slices were dried in air, followed by deparaffinization treatment and staining.

Next, a different fragment was dipped at 4° C. for 6 to 8 hours using a PLP fixative and then impregnated sequentially at 4° C. with PBS solutions having graded sucrose concentrations (duration: 4 hours with PBS having a 10% sucrose concentration, 4 hours with PBS having a 15% sucrose concentration, and overnight with PBS having 20% sucrose). Subsequently, the fragment was embedded in Tissue-Tek OCT compound (Sakura Finetechnical Co., Ltd.) and frozen in a dry ice/acetone bath. The frozen block was cut on a cryostat microtome into thin slices, and the thin sections were dried in air and then stored at −80° C. (method C).

The remaining one fragment was embedded at 4° C. in Tissue-Tek OCT compound and frozen in a dry ice/acetone bath. The frozen block was cut on a cryostat microtome into a plurality of thin sections, and the sections were then dried in air and fixed by the following different methods: one of the sections was fixed in 4% paraformaldehyde at 4° C. for 30 minutes (method D); a different section was fixed in acetone at 4° C. for 10 minutes (method E); and a different section was fixed in 10% neutral buffered formalin at room temperature for 30 minutes (method F). The sections fixed by the methods D, E, and F were washed for 5 minutes three times with Tris-buffered saline (TBS, 50 mM, pH 7.4), then dried in air and stored at −80° C.

The tissue sections thus prepared were used in immunohistochemical staining shown below. A GC33 antibody (IgG2a) and a 1G12 antibody (BioMosaic, IgG1) were used as primary antibodies at concentrations of 2.5 μg/ml and 1.0 μg/ml, respectively. For the staining, reagents included in LSAB-2 kit (DakoCytomation) were used as reagents necessary for staining. The staining method was conducted according to a method described in the instruction included in the kit. Antigen retrieval was not carried out because the fixation time was short. An antigen-antibody complex formed during the course of such immunohistochemical staining was visualized through peroxidase-diaminobenzidine (DAB) reaction. Hematoxylin was used in counter staining. In this context, control antibodies used for the primary antibodies were mouse IgG2 for GC33 and IgG1 for 1G12. Three cases were evaluated per method, and the results are shown in Table 1.

Stainability in the immunostaining was graded according to the following parameters:

regarding PR (rate of positive cells) grades, in the visual field under microscope using an objective lens with a magnification of 4 or 10, (i) when the proportion of cells from which the complex was detected was equal to or lower than 50%, the PR grade of the preparation was determined as "L",
(ii) when this proportion of cells from which the complex was detected was equal to or higher than 50% and lower than 70%, the PR grade of the preparation was determined as "ML",
(iii) when this proportion of cells from which the complex was detected was equal to or higher than 70% and lower than 90%, the PR grade of the preparation was determined as "MH", and
(iv) when this proportion of cells from which the complex was detected was equal to or higher than 90%, the PR grade of the preparation was determined as "H";

regarding SI (staining intensity scores),
(i) the SI score of a preparation that exhibited slightly positive staining was determined as "+1",
(ii) the SI score of a preparation that exhibited weakly positive staining was determined as "+2",
(iii) the SI score of a preparation that exhibited weakly positive staining with moderately or/and strongly positive staining was determined as "+3",
(iv) the SI score of a preparation that exhibited moderately positive staining was determined as "+4", and
(v) the SI score of a preparation that exhibited strongly positive staining was determined as "+5"; and regarding SP (cell membrane stainability) in the visual field under microscope using an objective lens with a magnification of 4 or 10,
(i) when only a portion of the cell membranes of cells was stained, the SP score of the preparation was determined as "I",
(ii) when a portion of the cell membranes of most of these cells was stained and the cell membranes of some of the cells were circumferentially stained, the SP score of the preparation was determined as "II", and
(iii) when the cell membranes of most of these cells were circumferentially stained, the SP score of the preparation was determined as "III".

Figure 2:
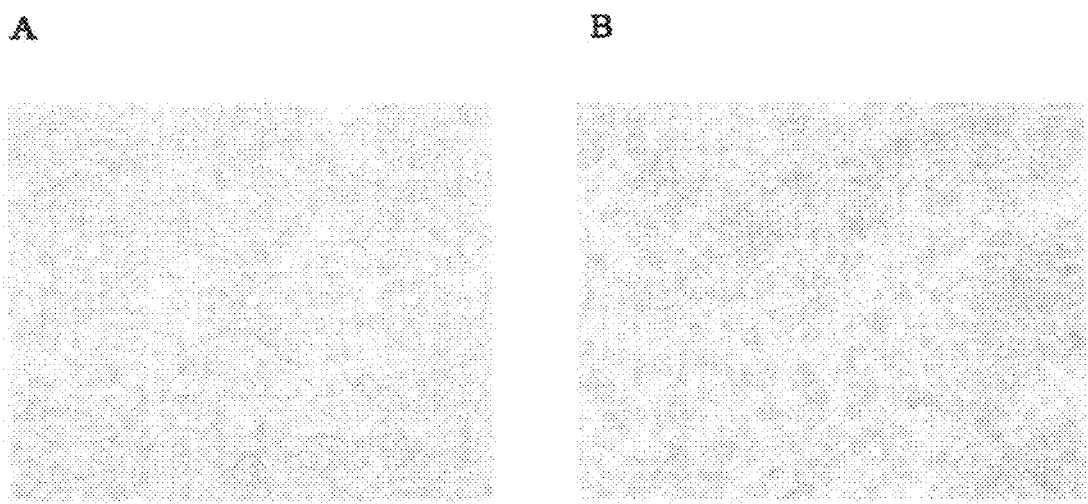
FIG. 2 is a diagram showing each grade of SP scores.

A standard stained image with each grade (+1, +2, +4, and +5) of the SI scores is shown in FIG. 1. FIG. 1A shows the preparation with SI of +1; FIG. 1B shows the preparation with SI of +2; FIG. 1C shows the preparation with SI of +4; and FIG. 1D shows the preparation with SI of +5. Moreover, a stained image with each grade (+I, +II, and +III) of the SP scores is shown in FIG. 2. FIG. 2A shows the preparation with SP of I, and FIG. 2B shows the preparation with SI of III.

The SI and SP grades of the preparations prepared by any of the methods C to F were both low, indicating that a sufficient stained image was not obtained. Moreover, the morphological structures of these preparations were not preserved. In the comparison between the methods A and B, the preparations prepared by the method B had high SI and SP grades (SI: +3 to +5, SP: II or III) and also had a PR grade in which 90% or more cells were determined to be positive (H). On the other

TABLE 1

| | PR | | | | | | | | SI | | | | | | | | | | SP | | | | | |
|---|---|---|---|---|---|---|---|---|---|---|---|---|---|---|---|---|---|---|---|---|---|---|---|---|
| | GC33 | | | | 1G12 | | | | GC33 | | | | | 1G12 | | | | | GC33 | | | 1G12 | | |
| | L | ML | MH | H | L | ML | MH | H | 1+ | 2+ | 3+ | 4+ | 5+ | 1+ | 2+ | 3+ | 4+ | 5+ | I | II | III | I | II | III |
| A | 0 | 1 | 2 | 0 | 1 | 2 | 0 | 0 | 0 | 1 | 2 | 0 | 0 | 2 | 1 | 0 | 0 | 0 | 2 | 1 | 0 | 3 | 0 | 0 |
| B | 0 | 0 | 0 | 3 | 0 | 0 | 0 | 3 | 0 | 0 | 0 | 0 | 3 | 0 | 0 | 1 | 2 | 0 | 0 | 0 | 3 | 0 | 2 | 1 |
| C | 0 | 0 | 0 | 3 | 0 | 0 | 0 | 3 | 3 | 0 | 0 | 0 | 0 | 3 | 0 | 0 | 0 | 0 | 3 | 0 | 0 | 3 | 0 | 0 |
| D | 0 | 0 | 0 | 3 | 0 | 0 | 0 | 3 | 3 | 0 | 0 | 0 | 0 | 3 | 0 | 0 | 0 | 0 | 3 | 0 | 0 | 3 | 0 | 0 |
| E | 0 | 0 | 0 | 3 | 0 | 0 | 0 | 3 | 3 | 0 | 0 | 0 | 0 | 3 | 0 | 0 | 0 | 0 | 3 | 0 | 0 | 3 | 0 | 0 |
| F | 0 | 0 | 0 | 3 | 0 | 0 | 0 | 3 | 3 | 0 | 0 | 0 | 0 | 3 | 0 | 0 | 0 | 0 | 3 | 0 | 0 | 3 | 0 | 0 |

A: 24-hour fixation, no antigen retrieval treatment
B: 24-hour fixation, antigen retrieval treatment using autoclave
C: 24-hour fixation, antigen retrieval treatment using microwave
D: 24-hour fixation, antigen retrieval treatment using protease treatment
E: 7-day fixation, no antigen retrieval treatment
F: 7-day fixation, antigen retrieval treatment using autoclave hand, the preparations prepared by the method A were determined to have SI of +3 to +5 and SP of I or II and also determined to have a PR grade of L to MH. In terms of the difference between the GC33 antibody and the 1G12 antibody, the GC33 antibody offered a stronger stained image in all the grades than that of the 1G12 antibody.

ing slightly more excellent SI and SP grades than those of the autoclave method. On the other hand, the preparations subjected to antigen retrieval treatment based on the protease method exhibited more excellent stainability in the PR grade and the SI and SP scores than that of the other preparations subjected to antigen retrieval treatment.

TABLE 2

| | PR | | | | | | | | SI | | | | | | | | | | SP | | | | | |
|---|---|---|---|---|---|---|---|---|---|---|---|---|---|---|---|---|---|---|---|---|---|---|---|---|
| | GC33 | | | | 1G12 | | | | GC33 | | | | | 1G12 | | | | | GC33 | | | 1G12 | | |
| | L | ML | MH | H | L | ML | MH | H | 1+ | 2+ | 3+ | 4+ | 5+ | 1+ | 2+ | 3+ | 4+ | 5+ | I | II | III | I | II | III |
| A | 0 | 1 | 2 | 0 | 1 | 2 | 0 | 0 | 0 | 1 | 2 | 0 | 0 | 2 | 1 | 0 | 0 | 0 | 2 | 1 | 0 | 3 | 0 | 0 |
| B | 0 | 0 | 0 | 3 | 0 | 0 | 0 | 3 | 0 | 2 | 1 | 0 | 3 | 0 | 0 | 1 | 2 | 0 | 3 | 0 | 0 | 1 | 2 | 0 |
| C | 0 | 0 | 0 | 3 | 0 | 0 | 0 | 3 | 0 | 1 | 0 | 2 | 0 | 0 | 0 | 1 | 2 | 0 | 1 | 2 | 0 | 1 | 2 | 0 |
| D | 0 | 0 | 0 | 3 | 0 | 0 | 0 | 3 | 0 | 0 | 0 | 0 | 3 | 0 | 0 | 0 | 0 | 3 | 3 | 0 | 0 | 0 | 1 | 2 |
| E | 2 | 1 | 0 | 0 | 1 | 2 | 0 | 0 | 1 | 2 | 0 | 0 | 0 | 2 | 0 | 1 | 0 | 0 | 3 | 0 | 0 | 3 | 0 | 0 |
| F | 1 | 0 | 0 | 2 | 0 | 0 | 0 | 3 | 2 | 0 | 1 | 0 | 0 | 0 | 2 | 0 | 1 | 0 | 8 | 0 | 0 | 2 | 1 | 0 |
| G | 0 | 0 | 1 | 2 | 0 | 0 | 0 | 3 | 0 | 2 | 0 | 1 | 0 | 0 | 0 | 2 | 1 | 0 | 2 | 1 | 0 | 2 | 1 | 0 |
| H | 0 | 0 | 0 | 3 | 0 | 0 | 0 | 3 | 0 | 0 | 0 | 2 | 1 | 0 | 0 | 0 | 3 | 0 | 0 | 2 | 1 | 0 | 3 | 0 |

A: 24-hour fixation, no antigen retrieval treatment
B: 24-hour fixation, antigen retrieval treatment using autoclave
C: 24-hour fixation, antigen retrieval treatment using microwave
D: 24-hour fixation, antigen retrieval treatment using protease treatment
E: 7-day fixation, no antigen retrieval treatment
F: 7-day fixation, antigen retrieval treatment using autoclave
G: 7-day fixation, antigen retrieval treatment using microwave
H: 7-day fixation, antigen retrieval treatment using protease treatment (5) Study on Fixation Time for Preparing Tumor Tissue Sections and Antigen Retrieval Method Uniform tissue grafts collected from the HepG2-transplanted models prepared in the paragraph (3) were studied for fixation time as follows: fixation time using 10% neutral buffered formalin in the method A described in the paragraph (4) was set to 24 hours and 7 days to prepare preparations. Moreover, the preparations prepared on each fixation time were respectively retrieved by any of retrieval methods using an autoclave, a microwave, or protease described below. Each preparation was treated with an autoclave at 121° C. for 10 minutes in a 10-fold dilution of target retrieval solution, pH 6 (DAKO) to prepare preparations retrieved with an autoclave. Moreover, each preparation was heated at 780 W for 5 minutes four times in the same solution to prepare preparations retrieved with a microwave. Furthermore, each preparation was reacted at room temperature for 5 minutes with AR reagent included in Histofine Her2 kit (MONO) (Nichirei Bioscience) to further prepare preparations.

The tissue sections thus prepared were used in immunohistochemical staining shown below. A GC33 antibody (IgG2a) and a 1G12 antibody (BioMosaic, IgG1) were used as primary antibodies at concentrations of 2.5 μg/ml and 1.0 μg/ml, respectively. For the staining, reagents included in LSAB-2 kit were used as reagents necessary for staining. The staining method was conducted according to a method described in the instruction included in the kit. Antigen retrieval was not carried out because the fixation time was short. An antigen-antibody complex formed during the course of such immunohistochemical staining was visualized through peroxidase-diaminobenzidine (DAB) reaction. Hematoxylin was used in counter staining. In this context, control antibodies used for the primary antibodies were mouse IgG2 for GC33 and IgG1 for 1G12. Three cases were evaluated per preparation to which each fixation time and each retrieval reaction were applied, and the results are shown in Table 2. In the comparison among the antigen retrieval methods, the microwave method produced the results show- (6) Immunohistochemical Staining of Tumor Tissue Sections
(6-1) Preparation and Staining of Tissue Preparations Tissue grafts collected from the transplanted models prepared in the paragraph (2) were dipped in 10% neutral buffered formalin for 7 days for fixation. Subsequently, paraffin-embedded block preparations of the tissue sections were prepared according to a standard method. The block preparations were cut into thin slices, and these tissue sections were used in immunohistochemical staining shown below.

A GC33 antibody (IgG2a) was used as a primary antibody. For the staining, reagents included in Histofine Her2 kit (MONO) (Nichirei Bioscience) were used as reagents necessary for staining. The staining method was conducted according to a method described in the instruction included in the kit except that the GC33 antibody was used as a primary antibody. In this context, antigen retrieval treatment was carried out by protease treatment (treatment involving reaction at room temperature for 5 minutes using protease included in the kit) or by autoclave treatment performed at 121° C. for 10 minutes in 10-fold diluted Target Retrieval Solution (Dako-Cytomation). An antigen-antibody complex formed during the course of such immunohistochemical staining was visualized through peroxidase-diaminobenzidine (DAB) reaction. Hematoxylin was used in counter staining. In this context, a control antibody used for the primary antibody was mouse IgG2.

(6-2) Evaluation of Staining Results

Stainability in the immunostaining using the mouse anti-human glypican 3 antibody was evaluated according to three parameters (rate of positive cells: PR, staining intensity: SI, and cell membrane staining pattern: SP) shown below.

Specifically, each parameter was digitized by the following methods:
the PR (rate of positive cells) scores were calculated such that: in the visual field under microscope using an objective lens with a magnification of 4 or 10,
(i) when the proportion of cells from which the complex is detected is zero, the score of the sample is 0, (ii) when this proportion is lower than 20%, the score of the sample is 1,
(iii) when this proportion is equal to or higher than 20% and lower than 50%, the score of the sample is 2, and
(iv) when this proportion is equal to or higher than 50%, the score of the sample is 3;

the SI–Cp (cytoplasmic staining intensity) scores reflecting cytoplasm stainability were calculated such that: in the cytoplasms of cells in the visual field under microscope,
(i) when the proportion of cells from which the complex is detected is zero using an objective lens with a magnification of 4 or 10 in the microscope, the score of the sample is 0,
(ii) when positive response, albeit obscure, is slightly observed using an objective lens with a magnification of 10 in the microscope, the score of the sample is 1,
(iii) when positive response is slightly observed using an objective lens with a magnification of 4, the score of the sample is 2,
(iv) when positive response is sufficiently recognizable even using an objective lens with a magnification of 4, the score of the sample is 3, and
(v) when strong positive response is clearly recognized and observed using an objective lens with a magnification of 4, the score of the sample is 4;

the SI–Cm (cell membrane staining intensity) scores reflecting cell membrane stainability were calculated such that: in the cell membranes of cells in the visual field under microscope,
(i) when the proportion of cells from which the complex is detected is zero using an objective lens with a magnification of 4 or 10 in the microscope, the score of the sample is 0,
(ii) when positive response, albeit obscure, is slightly observed using an objective lens with a magnification of 10 in the microscope, the score of the sample is 1,
(iii) when positive response obscure to an objective lens with a magnification of 4 but sufficiently recognizable using an objective lens with a magnification of 10 is observed, the score of the sample is 2,
(iv) when positive response is sufficiently recognizable even using an objective lens with a magnification of 4, the score of the sample is 3,
(v) when strong positive response is clearly recognized and observed using an objective lens with a magnification of 4, the score of the sample is 4; and the SP (cell membrane staining pattern) scores were calculated such that: in the detection of the complex in the cell membranes of cells in the visual field under microscope,
(i) when the cell membranes exhibit no positive response, the score of the sample is 0,
(ii) when less than 20% of cells exhibiting positive response exhibit complete membrane staining, the score of the sample is 1,
(iii) when 20% or more and less than 50% of cells exhibiting positive response exhibit complete membrane staining, the score of the sample is 2, and
(iv) when 50% or more of cells exhibiting positive response exhibit complete membrane staining, the score of the sample is 3.

The total score calculated using SI–Cm was indicated in $IR_{Cm}$, and the total score calculated using SI–Cp was indicated in $IR_{Cp}$.

(6-3) Evaluation of Stainability

Figure 3:
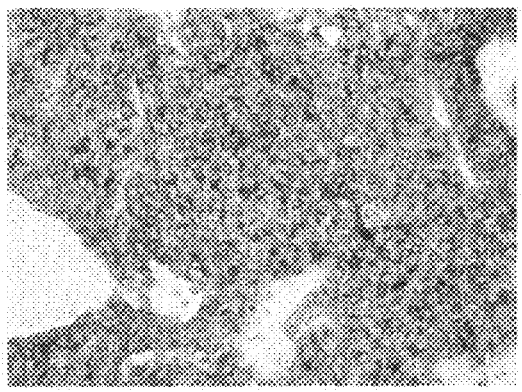
FIG. 3 is a diagram showing results of staining preparations derived from HuH-7 and HepG2 cell-transplanted models.
Figure 3:
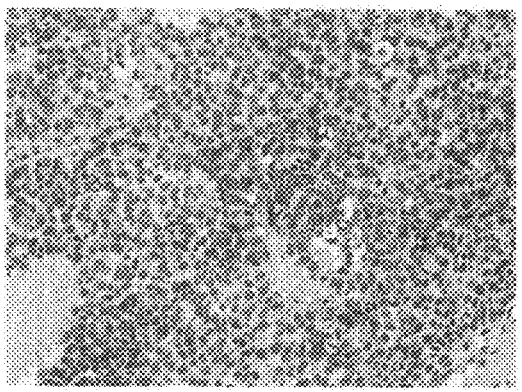
Figure 3:
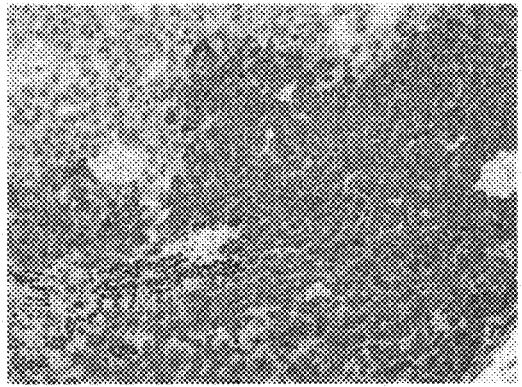
Figure 3:
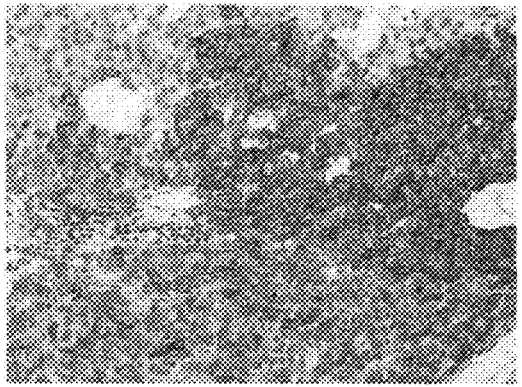

Stained images of the autoclave-treated tissue preparations derived from the HuH-7- and HepG2-transplanted animal models are shown in FIG. 3. FIG. 3A shows a stained image of a preparation obtained by subjecting a section prepared from the HuH-7-transplanted model to heat-induced epitope retrieval treatment using an autoclave; FIG. 3B shows a stained image of a preparation obtained by subjecting a section prepared from the HuH-7-transplanted model to protease-induced epitope retrieval treatment; FIG. 3C shows a stained image of a preparation obtained by subjecting a section prepared from the HepG2-transplanted model to heat-induced epitope retrieval treatment using an autoclave; and FIG. 3D shows a stained image of a preparation obtained by subjecting a section prepared from the HepG2-transplanted model to protease-induced epitope retrieval treatment.

Moreover, the scores of individual staining parameters are shown in Table 3. The $IR_{Cp}$ values calculated from the tissue preparations derived from the HuH-7- and HepG2-transplanted animal models were all 7, and no difference in the values was observed between HuH-7 and HepG2. Moreover, their $IR_{Cm}$ values were all 5, and no difference in the values was seen therebetween (Table 3 and FIG. 3).

TABLE 3

| Cell strain | Expression level per cell | Rate of positive cells | | Grade of cell membrane stainability | |
|---|---|---|---|---|---|
| | | Autoclave | Protease | Autoclave | Protease |
| HuH-7 | $1.25 \times 10^5$ | 90%< | 50%> | 1 | 2 |
| HepG2 | $9.67 \times 10^5$ | 90%< | 90%< | 2 | 3 |

On the other hand, the individual staining parameter scores of the protease-treated tissue preparations derived from the HuH-7- and HepG2-transplanted animal models are also shown in Table 3. The protease-treated tissue preparations were observed to tend to produce higher SI–Cm and SI–Cp scores than those obtained from the autoclave-treated preparations. In terms of the total scores calculated from the individual staining parameters, the $IR_{Cp}$ values obtained from the HuH-7- and HepG2-transplanted tissue preparations were 4 and 8, respectively. Moreover, the $IR_{Cm}$ values obtained from the HuH-7- and HepG2-transplanted tissue preparations were 4 and 9, respectively (Table 3 and FIG. 3). As shown in the lowest photograph of FIG. 3, the staining of the protease-treated tissue preparation can clearly distinguish cells expressing no glypican 3, cells moderately expressing glypican 3, and cells strongly expressing glypican 3. By contrast, the staining of the autoclave-treated tissue preparation did not produce such quantitative performance. Furthermore, non-specific reaction with inflammatory cells or the like was frequently observed in the staining of the autoclave-treated tissue preparation.

These results demonstrated that antigen retrieval based on protease treatment, compared with autoclave treatment, is a method more accurately reflecting the difference in the expression level of glypican 3. Moreover, it was shown that protease treatment is superior to autoclave treatment from the viewpoint of the stainability of cell membranes in tissue preparations.

Example 2

Antigen Retrieval Effect of Protease in GPC3 Immunostaining Using Human Hepatocellular Carcinoma Tissue Preparation (1) Immunohistochemical Staining of Human Hepatocellular Carcinoma Samples (1-1) Methods for Preparing and Staining Preparations Human hepatocellular carcinoma samples were dipped in 10% neutral buffered formalin for the predetermined time or longer for fixation. Next, paraffin-embedded block preparations were prepared according to a standard method. The block preparations were cut into thin slices, and these tissue sections were used in immunohistochemical staining. The immunohistochemical staining was carried out by the same procedures as in Example 1.

(1-2) Method for Evaluating Staining Results

On the basis of the description of the paragraph (6-2) of Example 1, stainability in the immunostaining using the mouse anti-human GPC3 antibody was evaluated according to three parameters (rate of positive cells: PR, staining intensity: SI, and cell membrane staining pattern: SP) shown below.

Specifically, each parameter was digitized by the following methods:

the PR (rate of positive cells) scores were calculated such that: in the visual field under microscope using an objective lens with a magnification of 4 or 10,
(i) when the proportion of cells from which the complex is detected is zero, the score of the sample is 0,
(ii) when this proportion is lower than 20%, the score of the sample is 1,
(iii) when this proportion is equal to or higher than 20% and lower than 50%, the score of the sample is 2, and
(iv) when this proportion is equal to or higher than 50%, the score of the sample is 3;

the SI–Cp (cytoplasmic staining intensity) scores reflecting cytoplasm stainability were calculated such that: in the cytoplasms of cells in the visual field under microscope,
(i) when the proportion of cells from which the complex is detected is zero using an objective lens with a magnification of 4 or 10 in the microscope, the score of the sample is 0,
(ii) when positive response, albeit obscure, is slightly observed using an objective lens with a magnification of 10 in the microscope, the score of the sample is 1,
(iii) when positive response is slightly observed using an objective lens with a magnification of 4, the score of the sample is 2,
(iv) when positive response is sufficiently recognizable even using an objective lens with a magnification of 4, the score of the sample is 3, and
(v) when strong positive response is clearly recognized and observed using an objective lens with a magnification of 4, the score of the sample is 4;

the SI–Cm (cell membrane staining intensity) scores reflecting cell membrane stainability were calculated such that: in the cell membranes of cells in the visual field under microscope,
(i) when the proportion of cells from which the complex is detected is zero using an objective lens with a magnification of 4 or 10 in the microscope, the score of the sample is 0,
(ii) when positive response, albeit obscure, is slightly observed using an objective lens with a magnification of 10 in the microscope, the score of the sample is 1,
(iii) when positive response obscure to an objective lens with a magnification of 4 but sufficiently recognizable using an objective lens with a magnification of 10 is observed, the score of the sample is 2,
(iv) when positive response is sufficiently recognizable even using an objective lens with a magnification of 4, the score of the sample is 3,
(v) when strong positive response is clearly recognized and observed using an objective lens with a magnification of 4, the score of the sample is 4; and the SP (cell membrane staining pattern) scores were calculated such that: in the detection of the complex in the cell membranes of cells in the visual field under microscope,
(i) when the cell membranes exhibit no positive response, the score of the sample is 0,
(ii) when less than 20% of cells exhibiting positive response exhibit complete membrane staining, the score of the sample is 1,
(iii) when 20% or more and less than 50% of cells exhibiting positive response exhibit complete membrane staining, the score of the sample is 2, and
(iv) when 50% or more of cells exhibiting positive response exhibit complete membrane staining, the score of the sample is 3.

Moreover, the degree of non-specific staining (background) (determined from stainability of inflammatory cells or stromata) was also evaluated.

(1-3) Results and Conclusion

Figure 4:
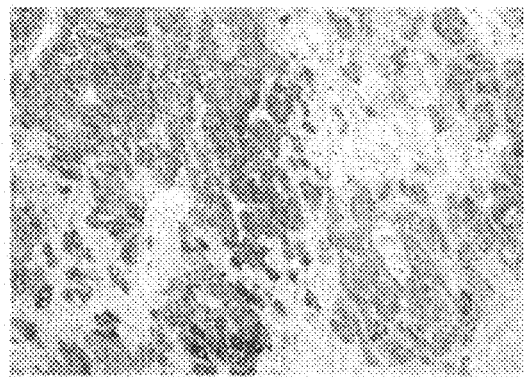
FIG. 4 is a diagram showing results of staining preparations prepared from clinical samples of human liver cancer.
Figure 4:
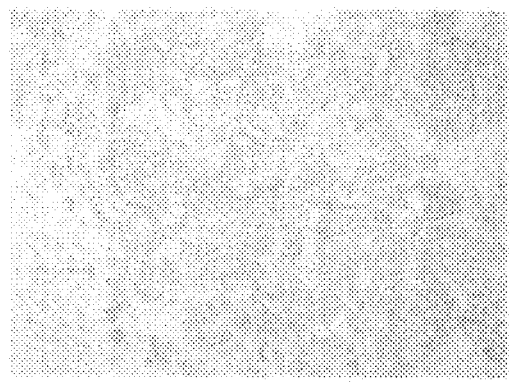
Figure 4:
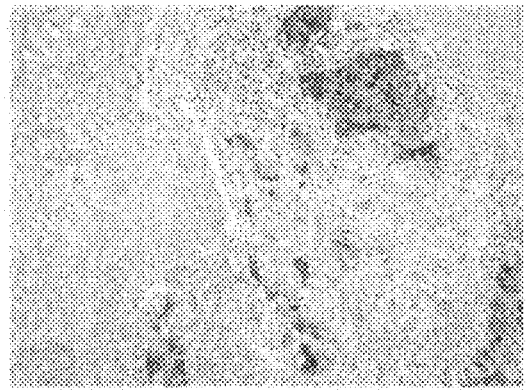
Figure 4:
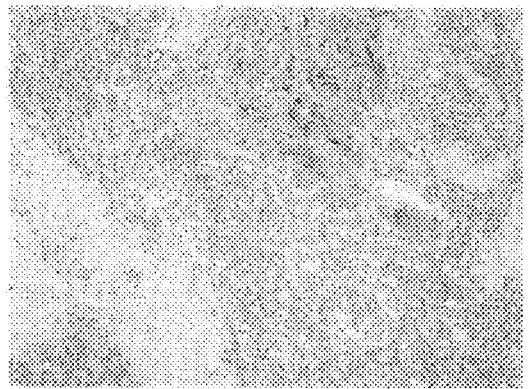
Figure 4:
Figure 4:
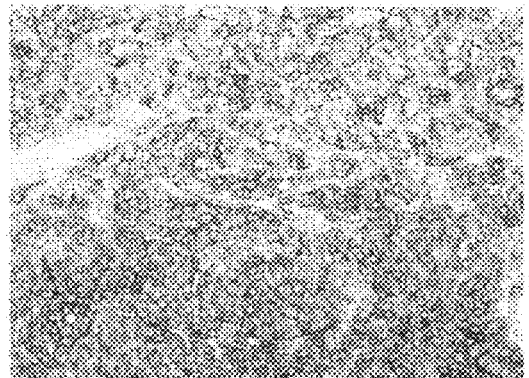

Stained images of the preparations subjected to antigen retrieval treatment are shown in FIG. 4. FIG. 4A shows a stained image of a preparation obtained by subjecting a section prepared from the sample of case A to heat-induced epitope retrieval treatment using an autoclave; FIG. 4B shows a stained image of a preparation obtained by subjecting a section prepared from the sample of case A to protease-induced epitope retrieval treatment; FIG. 4C shows a stained image of a preparation obtained by subjecting a section prepared from the sample of case B to heat-induced epitope retrieval treatment using an autoclave; FIG. 4D shows a stained image of a preparation obtained by subjecting a section prepared from the sample of case B to protease-induced epitope retrieval treatment; FIG. 4E shows a stained image of a preparation obtained by subjecting a section prepared from the sample of case C to heat-induced epitope retrieval treatment using an autoclave; and FIG. 4F shows a stained image of a preparation obtained by subjecting a section prepared from the sample of case C to protease-induced epitope retrieval treatment.

As shown in FIG. 4 and Table 4, the hepatocellular carcinoma regions in the diagram had a PR score of 3 (50% or more of the region was positive) in all the autoclave-treated tissue preparations of the cases A, B, and C. Moreover, no membrane localization was seen in the cases A and B as to the intensity and pattern of membrane staining (SI–Cm=0 and SP–Cm=0), whereas expression in the membrane was observed in the case C with scores of SI–Cm=1 and SP–Cm=2. In this context, all the cases tended to exhibit non-specific positive response to inflammatory cells or stromata, as shown in the photograph of the case B in FIG. 4.

TABLE 4

| Parameter | Antigen retrieval method | Case A | Case B | Case C |
|---|---|---|---|---|
| PR | Autoclave | 3 | 3 | 3 |
|  | Protease | 1 | 2 | 3 |

TABLE 4-continued

| Parameter | Antigen retrieval method | Case A | Case B | Case C |
|---|---|---|---|---|
| SI-CP | Autoclave | 3 | 3 | 3 |
|  | Protease | 1 | 2 | 3 |
| SI-CM | Autoclave | 0 | 0 | 1 |
|  | Protease | 1 | 3 | 4 |
| SP | Autoclave | 0 | 0 | 2 |
|  | Protease | 1 | 2 | 3 |

On the other hand, the PR scores of the protease-treated tissue preparations were 1 (less than 20% of the region was positive) in the case A, 2 (20-50% of the region was positive) in the case B, and 3 (50% or more of the region was positive) in the case C. Moreover, the scores of the case A were SI–Cm=1 and SP–Cm=1 as to the intensity and pattern of membrane staining. Moreover, the scores of the case B were SI–Cm=3 and SP–Cm=2. Distinct expression in the membrane was observed in the case C with scores of SI–Cm=4 and SP–Cm=3. Unlike the autoclave-treated tissue preparations, little non-specific positive response was observed in the protease-treated tissue preparations.

These results suggested that antigen retrieval method based on protease treatment, compared with autoclave treatment, is probably a method more accurately reflecting the difference in the expression level of GPC3 in GPC3 immunostaining using clinical samples of hepatocellular carcinoma. Moreover, it was shown that protease treatment is also superior thereto in cell membrane stainability. Furthermore, it was demonstrated that the protease method produces only minimum non-specific positive response and can therefore more precisely capture specific positive response to an anti-GPC3 antibody.

Example 3

Drug Efficacy of Anti-GPC3 Antibody on GPC3-Expressing Human Liver Cancer Cell Strain-Transplanted Mouse Models (1) Cell Strain Cells used in transplantation were HuH-7 cells and HepG2 cells. The HuH-7 cells were maintained and subcultured in Dulbecco's Modified Eagle's Medium (SIGMA-ALDRICH CO.) containing 10% FBS (BIONET). The HepG2 cells were maintained and subcultured in Minimum Essential Medium Eagle medium (SIGMA-ALDRICH CO.) containing 10% FBS, 1 mmol/l MEM Sodium Pyruvate (Invitrogen Corp.), and 1 mmol/l MEM Non-Essential Amino Acid (Invitrogen Corp.).

(2) Preparation of Human Liver Cancer Cell Strain-Transplanted Mouse Models

The cells of these strains were separately adjusted to $5 \times 10^7$ cells per ml with a solution containing equal amounts of the medium for maintenance and subculture described above and Matrigel Matrix (BD Biosciences). One day before cell transplantation, 100 μl of an anti-asialo GM1 antibody (Wako Pure Chemical Industries, Ltd.; 1 vial was dissolved in 5 ml of PBS) was intraperitoneally administered in advance to SCID mice (5-week-old male, CLEA Japan, Inc.), and 100 μl of each cell suspension was subcutaneously transplanted to the abdominal regions of the mice. Specifically, $5 \times 10^6$ cells were administered per mouse. The tumor volumes were calculated according to the following equation, and the models were regarded as being established at the point in time when the average of tumor volumes reached 117 to 330 mm³:

$$\text{Tumor volume} = \text{Major axis} \times \text{Minor axis} \times \text{Minor axis}/2. \quad \text{Equation 1}$$

(3) Preparation of Antibody to be Administered

On the day of administration, a humanized anti-human GPC3 monoclonal antibody (clone name: hGC33, described in International Publication No. WO2006/006693) was adjusted as a therapeutic antibody to 0.5 mg/ml, 0.1 mg/ml, or 0.05 mg/ml with filter-satirized PBS and used as an administration sample to a 5 mg/kg-administered group, a 1 mg/kg-administered group, or a 0.5 mg/kg-administered group, respectively.

(4) Antibody Administration

Twenty days after the transplantation in the HuH-7 cell-transplanted mouse models prepared as described in the paragraph (2) or 26 days after the transplantation in the HepG2 cell-transplanted mouse models thus prepared, the administration sample prepared in the preceding paragraph (3) was administered at a dose of 10 ml/kg from the tail veins for 3 weeks on a once-a-week basis. Filter-sterilized PBS (vehicle) was administered as a negative control at a dose of 10 ml/kg from the tail veins for 3 weeks on a once-a-week basis in the same way as above. All the groups were composed of 5 to 6 mice per group.

(5) Evaluation of Antitumor Effect

Figure 5A:
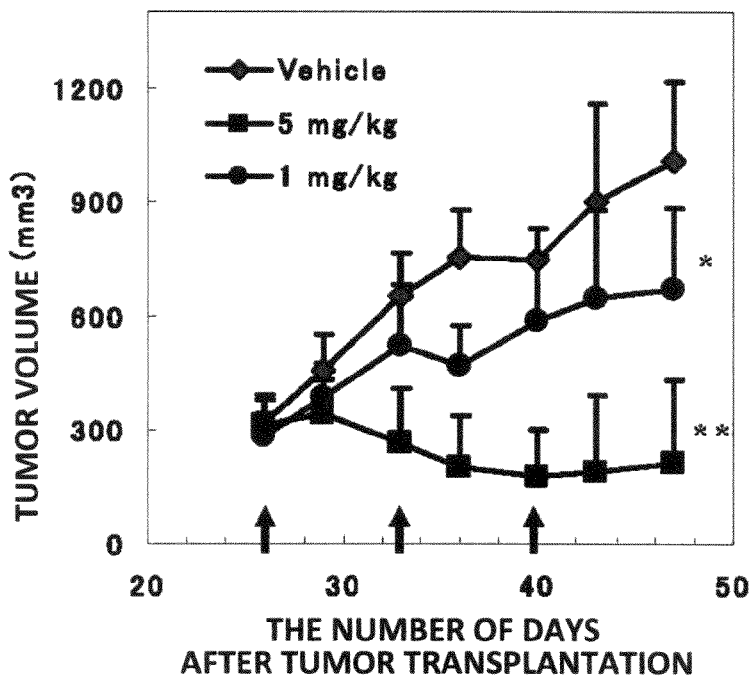
FIG. 5A is a diagram showing the antitumor effect of an hGC33 antibody on human liver cancer-transplanted mouse models.
Figure 5B:
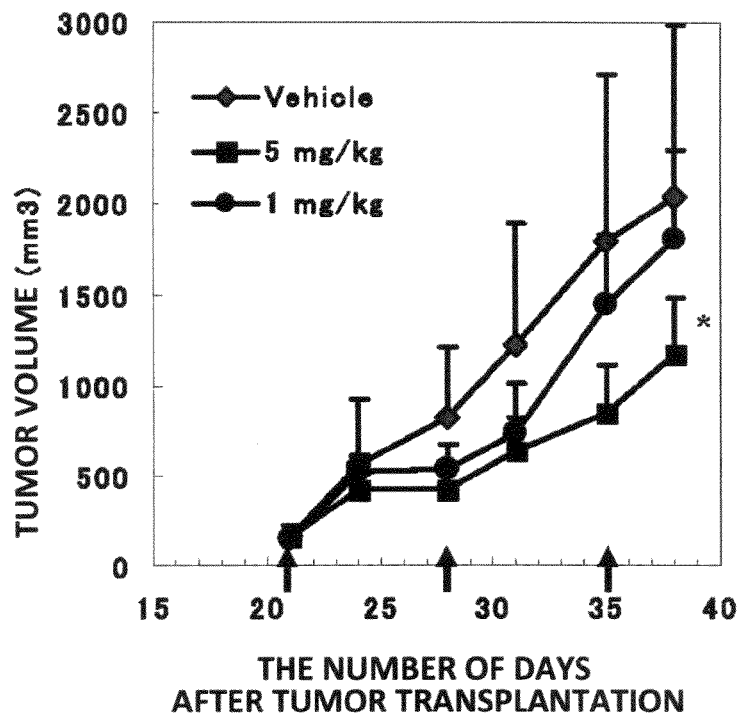
FIG. 5B is a diagram showing the antitumor effect of an hGC33 antibody on human liver cancer-transplanted mouse models.
Figure 5C:
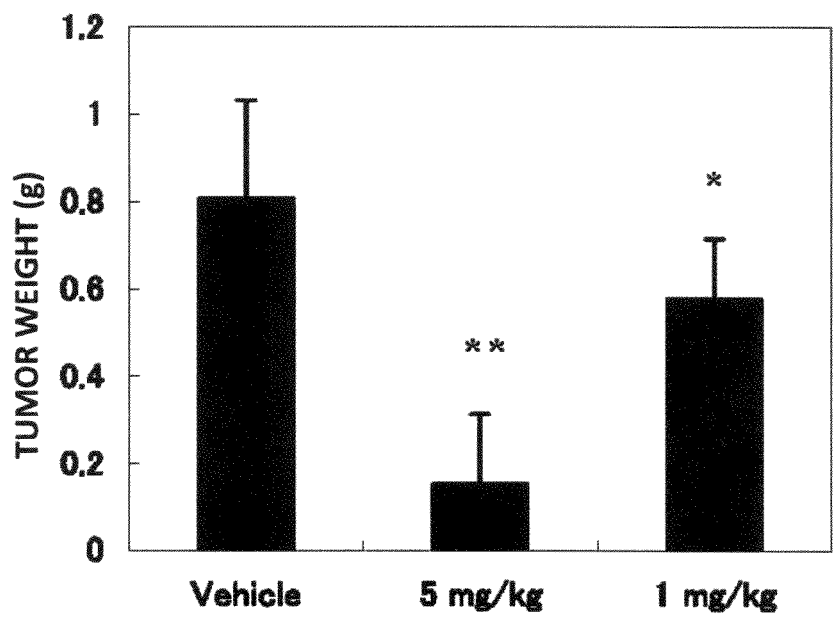
FIG. 5C is a diagram showing the antitumor effect of an hGC33 antibody on human liver cancer-transplanted mouse models.
Figure 5D:
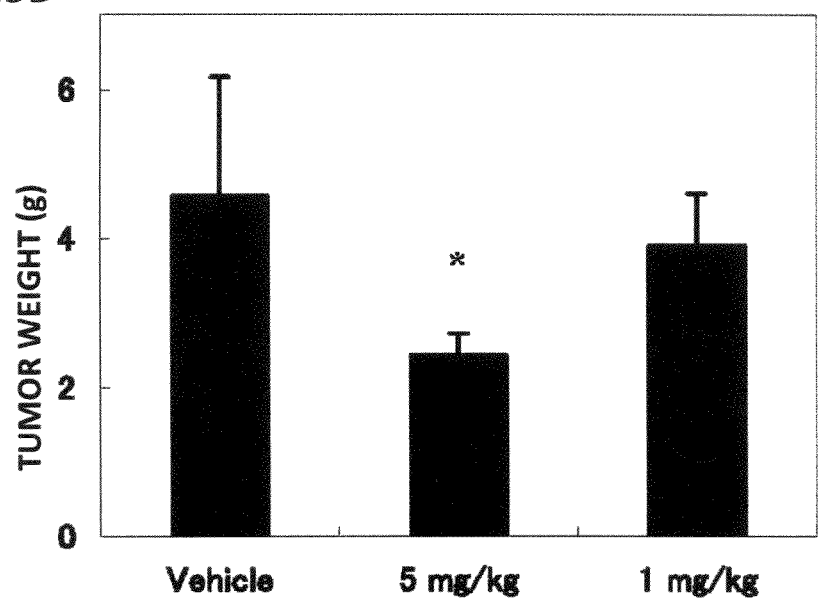
FIG. 5D is a diagram showing the antitumor effect of an hGC33 antibody on human liver cancer-transplanted mouse models.

The antitumor effect of the hGC33 antibody on the human liver cancer-transplanted mouse models was evaluated on the basis of time-dependent change in the tumor volumes (FIG. 5A) and the wet volumes of tumors after 1 week from the final administration day (FIG. 5B). FIG. 5A is a diagram showing time-dependent change in tumor volumes of the HepG2-transplanted mouse models. The rhombus represents time-dependent change in the tumor volumes of the vehicle-administered group; the square represents time-dependent change in the tumor volumes of the 1 mg/kg hGC33 antibody-administered group; and the circle represents time-dependent change in the tumor volumes of the 5 mg/kg hGC33 antibody-administered group. The point in time when the hGC33 antibody was administered is indicated in the arrow. In the diagram, the symbol * represents that the significance level P is $P<0.05$ in the significant difference test. Moreover, the symbol ** represents that the significance level P is $P<0.0001$ in the significant difference test. FIG. 5B is a diagram showing time-dependent change in the tumor volumes of the HuH-7-transplanted mouse models. The rhombus represents time-dependent change in the tumor volumes of the vehicle-administered group; the square represents time-dependent change in the tumor volumes of the 1 mg/kg hGC33 antibody-administered group; and the circle represents time-dependent change in the tumor volumes of the 5 mg/kg hGC33 antibody-administered group. The point in time when the hGC33 antibody was administered is indicated in the arrow. In the diagram, the symbol * represents that the significance level P is $P<0.05$ in the significant difference test. Moreover, the symbol ** represents that the significance level P is $P<0.0001$ in the significant difference test. FIG. 5C is a diagram showing the wet volumes of tumors after 1 week from the final administration day in the HepG2-transplanted mouse models. In the diagram, the symbol * represents that the significance level P is $P<0.05$ in the significant difference test. Moreover, the symbol ** represents that the significance level P is $P<0.0001$ in the significant difference test. FIG. 5D is a diagram showing the wet volumes of tumors after 1 week from the final administration day in the HuH-7-transplanted mouse models. In the diagram, the symbol * represents that the significance level P is $P<0.05$ in the significant difference test. Moreover, the symbol ** represents that the significance level P is $P<0.0001$ in the significant difference test.

SAS preclinical package (SAS Institute, Inc.) was used in the statistical analysis. The tumor volumes obtained on the final measurement day were used to evaluate the significant difference test by Dunnett multiple comparison method. As a result, as shown in FIGS. 5A and 5B, tumor growth in the hGC33 antibody-administered groups was confirmed to be significantly suppressed, compared with that in the vehicle-administered group. Moreover, the drug efficacy of the antibody was demonstrated to be relatively strong in the HepG2 cell-transplanted models and relatively weak in the HuH-7 cell-transplanted models.

Thus, the antibody was demonstrated to exhibit high antitumor effect on HepG2 cell-transplanted mouse models determined to exhibit a high expression level of the antigen and the expression pattern of cell membrane localization as a result of analyzing, by immunohistological staining, tissue preparations prepared by protease-induced epitope retrieval method. By contrast, the antibody was demonstrated to exhibit low antitumor effect on HuH-7 cell-transplanted mouse models determined from the analysis results to have a low expression level of the antigen. Such difference is a conclusion that cannot be reached by analysis based on the conventional heat-induced epitope retrieval method. It was thus shown that the drug efficacy of the GPC3 antibody can be determined effectively by combining the conventional heat-induced epitope retrieval method with protease-induced epitope retrieval method.

All publications, patents, and patent applications cited herein are incorporated herein by reference in their entirety.

The invention claimed is:

1. An in-vitro immunoassay method for detecting the presence of liver cancer cells in a subject, comprising the steps of:
    (a) providing a set of at least two identifiable liver tissue preparations as paraffin embedded sections from the same subject, the identifiable liver tissue preparations being prepared from the subject, then embedded in paraffin and attached to a transparent support;
    (b) subjecting the set of the liver tissue preparations to deparaffinization treatment;
    (c) subjecting one of the identifiable liver tissue preparations in the set treated in the step (b) to antigen retrieval treatment based on heat-induced epitope retrieval method, while subjecting the other liver tissue preparation to antigen retrieval treatment based on protease-induced epitope retrieval method;
    (d) contacting an anti-glypican 3 antibody with the preparations under conditions appropriate for formation of a complex of the anti-glypican 3 antibody with glypican 3 present in the liver tissue preparations treated in the step (c); and
    (e) detecting the presence of the complex by using immunohistochemistry, wherein when the complex is present, the subject is diagnosed as having liver cancer cells.

2. The method according to claim 1, wherein the heat-induced epitope retrieval method is heating using a microwave.

3. The method according to claim 1, wherein the heat-induced epitope retrieval method is heating using an autoclave.

4. The method according to claim 1, wherein the protease used in the protease-induced epitope retrieval method is selected from the group consisting of pepsin, trypsin, and protease K.

5. The method according to claim 1, wherein detection reaction for detecting the complex is enzymatic reaction.

6. The method according to claim 1, wherein the anti-glypican 3 antibody is an antibody binding to a C-terminal polypeptide of glypican 3.

7. The method according to claim 6, wherein the C-terminal polypeptide of glypican 3 is a polypeptide consisting of amino acids at positions 359 to 580 described in SEQ ID NO: 1 or a polypeptide consisting of amino acids at positions 375 to 580 therein.

8. The method according to claim 7, wherein the anti-glypican 3 antibody is a GC33 antibody.

9. The method according to claim 1, wherein the anti-glypican 3 antibody is a 1G12 antibody.

10. The method according to claim 1, wherein in the step (e), the presence of the complex is digitized for detection.

11. The method according to claim 10, wherein the digitization is performed by calculation according to the following formula:

$$IR_{Cp} = PR + (SI-Cp) + SP$$

wherein $IR_{Cp}$ represents an expression level score of glypican 3;

PR represents a numeric value determined by scoring the proportion of cells from which the complex is detected under microscope;

SI–Cp represents a numeric value determined by scoring staining intensity with which the complex is detected in the cytoplasms of cells in the visual field under microscope; and SP represents a numeric value determined by scoring the proportion of cells that exhibit complete membrane staining in the cell membranes of cells in the visual field under microscope.

12. The method according to claim 10, wherein the digitization is performed by calculation according to the following formula:

$$IR_{Cm} = PR + (SI-Cm) + SP$$

wherein $IR_{Cm}$ represents a membrane localization score of glypican 3;

PR represents a numeric value determined by scoring the proportion of cells from which the complex is detected under microscope;

SI–Cm represents a numeric value determined by scoring staining intensity with which the complex is detected in the cell membranes of cells in the visual field under microscope; and SP represents a numeric value determined by scoring the proportion of cells that exhibit complete membrane staining in the cell membranes of cells in the visual field under microscope.

* * * * *